(12) United States Patent
Keiser et al.

(10) Patent No.: US 8,449,578 B2
(45) Date of Patent: May 28, 2013

(54) MULTIPLANAR BONE ANCHOR SYSTEM

(75) Inventors: Matthew L. Keiser, Hillsdale, NJ (US); Laurie G. Sanders, Glen Ridge, NJ (US); Christopher Shaffrey, Charlottesville, VA (US)

(73) Assignee: EBI, LLC, Parsippany, NJ (US)

( * ) Notice: Subject to any disclaimer, the term of this patent is extended or adjusted under 35 U.S.C. 154(b) by 514 days.

(21) Appl. No.: 12/614,734

(22) Filed: Nov. 9, 2009

(65) Prior Publication Data
US 2011/0112578 A1 May 12, 2011

(51) Int. Cl.
*A61B 17/70* (2006.01)

(52) U.S. Cl.
USPC ........... 606/264; 606/267; 606/269; 606/270; 606/305

(58) Field of Classification Search
USPC .................................. 606/264–275, 300–321
See application file for complete search history.

(56) References Cited

U.S. PATENT DOCUMENTS

| | | | |
|---|---|---|---|
| 5,209,753 A | 5/1993 | Biedermann et al. | |
| 5,291,075 A | 3/1994 | Hollstein et al. | |
| 5,360,431 A * | 11/1994 | Puno et al. | 606/308 |
| 5,454,813 A | 10/1995 | Lawes | |
| 5,466,237 A | 11/1995 | Byrd, III et al. | |
| 5,499,983 A * | 3/1996 | Hughes | 606/267 |
| 5,713,900 A | 2/1998 | Benzel et al. | |
| 5,876,402 A | 3/1999 | Errico et al. | |
| 5,908,422 A | 6/1999 | Bresina | |
| 6,063,090 A | 5/2000 | Schlapfer | |
| 6,074,391 A | 6/2000 | Metz-Stavenhagen et al. | |
| 6,090,111 A | 7/2000 | Nichols | |
| 6,280,442 B1 | 8/2001 | Barker et al. | |
| 6,315,779 B1 * | 11/2001 | Morrison et al. | 606/281 |
| RE37,665 E | 4/2002 | Ralph et al. | |
| 6,406,477 B1 | 6/2002 | Fujiwara | |
| 6,443,954 B1 | 9/2002 | Bramlet et al. | |
| 6,478,798 B1 * | 11/2002 | Howland | 606/264 |

(Continued)

FOREIGN PATENT DOCUMENTS

| | | |
|---|---|---|
| CA | 2289629 A1 | 11/1998 |
| DE | 19509332 C1 | 8/1996 |

(Continued)

OTHER PUBLICATIONS

Burkus, MD, Kenneth, Medtronic, TSRH-3D Spinal System, Surgical Technique, 2009, pp. 32.

(Continued)

*Primary Examiner* — Eduardo C Robert
*Assistant Examiner* — Jerry Cumberledge
(74) *Attorney, Agent, or Firm* — Harness, Dickey

(57) ABSTRACT

The present teachings provide one or more surgical implements for repairing damaged tissue, such as in the case of a spinal fixation procedure. A multiplanar bone anchor system for a fixation procedure is provided. The system can include a bone fastener. The bone fastener can include a head and a second end adapted to engage an anatomy. The bone fastener can extend along a longitudinal axis. The system can also include a coupling arrangement coupled to the head of the bone fastener so that the bone fastener is rotatable about the longitudinal axis to define a first plane of motion. The system can further include a saddle, which can be coupled to the coupling arrangement. The saddle can be movable relative to at least one of the bone fastener and the coupling arrangement to define a second plane of motion.

39 Claims, 19 Drawing Sheets

U.S. PATENT DOCUMENTS

| | | |
|---|---|---|
| 6,520,963 B1 | 2/2003 | McKinley |
| 6,660,004 B2 | 12/2003 | Barker et al. |
| 6,685,705 B1 | 2/2004 | Taylor |
| 6,736,820 B2 | 5/2004 | Biedermann et al. |
| 6,974,460 B2 | 12/2005 | Carbone et al. |
| RE39,089 E | 5/2006 | Ralph et al. |
| 7,081,116 B1 | 7/2006 | Carly |
| 7,081,117 B2 | 7/2006 | Bono et al. |
| 7,087,057 B2 | 8/2006 | Konieczynski et al. |
| 7,306,602 B2 | 12/2007 | Bono et al. |
| 7,322,981 B2 | 1/2008 | Jackson |
| 7,445,627 B2 | 11/2008 | Hawkes et al. |
| 7,572,279 B2 | 8/2009 | Jackson |
| 7,578,833 B2 | 8/2009 | Bray |
| 7,591,839 B2 | 9/2009 | Biedermann et al. |
| 7,635,380 B2 * | 12/2009 | Zucherman et al. .......... 606/267 |
| 7,691,131 B2 | 4/2010 | Graf |
| 7,699,876 B2 | 4/2010 | Barry et al. |
| 7,704,270 B2 * | 4/2010 | De Coninck .................. 606/264 |
| 7,731,734 B2 | 6/2010 | Clement et al. |
| 7,749,258 B2 | 7/2010 | Biedermann et al. |
| 7,780,706 B2 * | 8/2010 | Marino et al. ............... 606/264 |
| 7,811,310 B2 * | 10/2010 | Baker et al. .................. 606/267 |
| 7,850,718 B2 * | 12/2010 | Bette et al. ................... 606/267 |
| 7,850,719 B2 | 12/2010 | Gournay et al. |
| 7,857,834 B2 | 12/2010 | Boschert |
| 7,922,748 B2 | 4/2011 | Hoffman |
| 7,955,358 B2 | 6/2011 | Albert |
| 7,967,849 B2 | 6/2011 | Carson et al. |
| 8,012,183 B2 * | 9/2011 | Alain ............................ 606/264 |
| 2001/0001119 A1 | 5/2001 | Lombardo |
| 2004/0102781 A1 * | 5/2004 | Jeon ................................ 606/73 |
| 2004/0177847 A1 * | 9/2004 | Foley et al. .................. 128/95.1 |
| 2005/0080420 A1 | 4/2005 | Farris et al. |
| 2005/0203515 A1 | 9/2005 | Doherty et al. |
| 2005/0203516 A1 | 9/2005 | Biedermann et al. |
| 2005/0234451 A1 * | 10/2005 | Markworth ..................... 606/61 |
| 2006/0264933 A1 * | 11/2006 | Baker et al. ..................... 606/61 |
| 2007/0118123 A1 | 5/2007 | Strausbaugh et al. |
| 2007/0233063 A1 | 10/2007 | Rezach |
| 2007/0274800 A1 * | 11/2007 | Mikkonen et al. ............... 411/15 |
| 2008/0004623 A1 | 1/2008 | Ferrante et al. |
| 2008/0009862 A1 | 1/2008 | Hoffman |
| 2008/0077138 A1 | 3/2008 | Cohen et al. |
| 2008/0108992 A1 * | 5/2008 | Barry et al. ..................... 606/61 |
| 2008/0119857 A1 | 5/2008 | Potash et al. |
| 2008/0125816 A1 | 5/2008 | Jackson |
| 2008/0140135 A1 | 6/2008 | Konieczynski et al. |
| 2008/0154315 A1 | 6/2008 | Jackson |
| 2008/0161853 A1 | 7/2008 | Arnold et al. |
| 2008/0161863 A1 | 7/2008 | Arnold et al. |
| 2008/0177260 A1 | 7/2008 | McKinley et al. |
| 2008/0195159 A1 * | 8/2008 | Kloss et al. .................... 606/305 |
| 2008/0243193 A1 | 10/2008 | Ensign et al. |
| 2008/0249570 A1 | 10/2008 | Carson et al. |
| 2008/0262497 A1 | 10/2008 | Nijenbanning et al. |
| 2008/0262548 A1 * | 10/2008 | Lange et al. .................. 606/256 |
| 2008/0269809 A1 | 10/2008 | Garamszegi |
| 2008/0287994 A1 * | 11/2008 | Perez-Cruet et al. ......... 606/246 |
| 2008/0312655 A1 | 12/2008 | Kirschman et al. |
| 2009/0024155 A1 | 1/2009 | Lee-Sepsick et al. |
| 2009/0036929 A1 | 2/2009 | Reglos et al. |
| 2009/0076552 A1 | 3/2009 | Tornier |
| 2009/0105769 A1 | 4/2009 | Rock et al. |
| 2009/0182384 A1 * | 7/2009 | Wilcox et al. ................. 606/305 |
| 2009/0210015 A1 * | 8/2009 | Cermak et al. ................ 606/305 |
| 2009/0248025 A1 | 10/2009 | Haidukewych et al. |
| 2010/0036426 A1 | 2/2010 | Mitchell et al. |
| 2010/0100137 A1 | 4/2010 | Justis et al. |
| 2010/0198272 A1 | 8/2010 | Keyer et al. |
| 2010/0204735 A1 * | 8/2010 | Gephart et al. ............... 606/264 |
| 2010/0228293 A1 | 9/2010 | Courtney et al. |
| 2010/0241170 A1 | 9/2010 | Cammisa et al. |
| 2010/0268279 A1 | 10/2010 | Gabelberger et al. |
| 2010/0305621 A1 | 12/2010 | Wang et al. |
| 2011/0093021 A1 | 4/2011 | Fanger et al. |
| 2011/0106173 A1 | 5/2011 | Lindemann et al. |
| 2011/0106175 A1 | 5/2011 | Rezach |
| 2011/0106176 A1 | 5/2011 | Jackson |
| 2011/0106180 A1 | 5/2011 | Miller et al. |
| 2011/0137348 A1 | 6/2011 | Jackson |

FOREIGN PATENT DOCUMENTS

| | | |
|---|---|---|
| DE | 19720782 A1 | 11/1998 |
| EP | 0441729 A1 | 8/1991 |
| WO | WO-9702786 A1 | 1/1997 |
| WO | WO-9852482 A1 | 11/1998 |
| WO | WO-0115612 A1 | 3/2001 |
| WO | WO-2005122929 A1 | 12/2005 |
| WO | WO-2006009753 A1 | 1/2006 |
| WO | WO-2007047711 A2 | 4/2007 |
| WO | 2008042948 A2 | 4/2008 |
| WO | WO-2008057551 A2 | 5/2008 |
| WO | 2009055407 | 4/2009 |
| WO | 2010090428 A2 | 8/2010 |

OTHER PUBLICATIONS

EBI Spine, Polaris, Surgical Technique, 2006, pp. 28.
EBI, A Biomet Company, Omega 21 Spinal Fixation System, EBI Spine System, 2001.
Medtronic, Vertex Max, Reconstruction System Surgical Technique Demonstrating Occipital Plate Rod and Occipital Keel Plate, 2009, pp. 1-44.
International Search Report and Written Opinion for PCT/US2010/054453 Mailed Jun. 28, 2011.
DePuy Spinen™, Mountaineer™ OCT Spinal System, Surgical Technique. ©2005 DePuy Spine, Inc.
International Search Report and Written Opinion for Application No. PCT/US2012/036234 mailed Nov. 16, 2012.

* cited by examiner

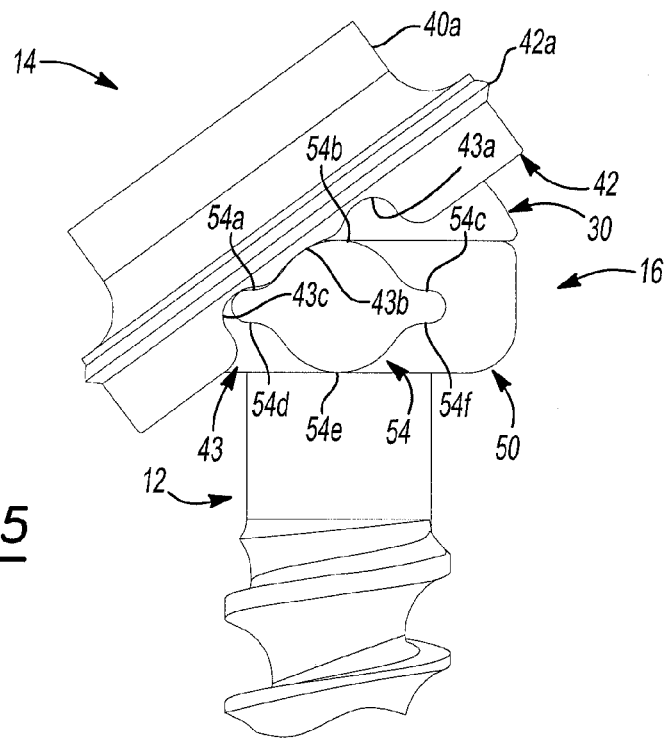
Fig-5
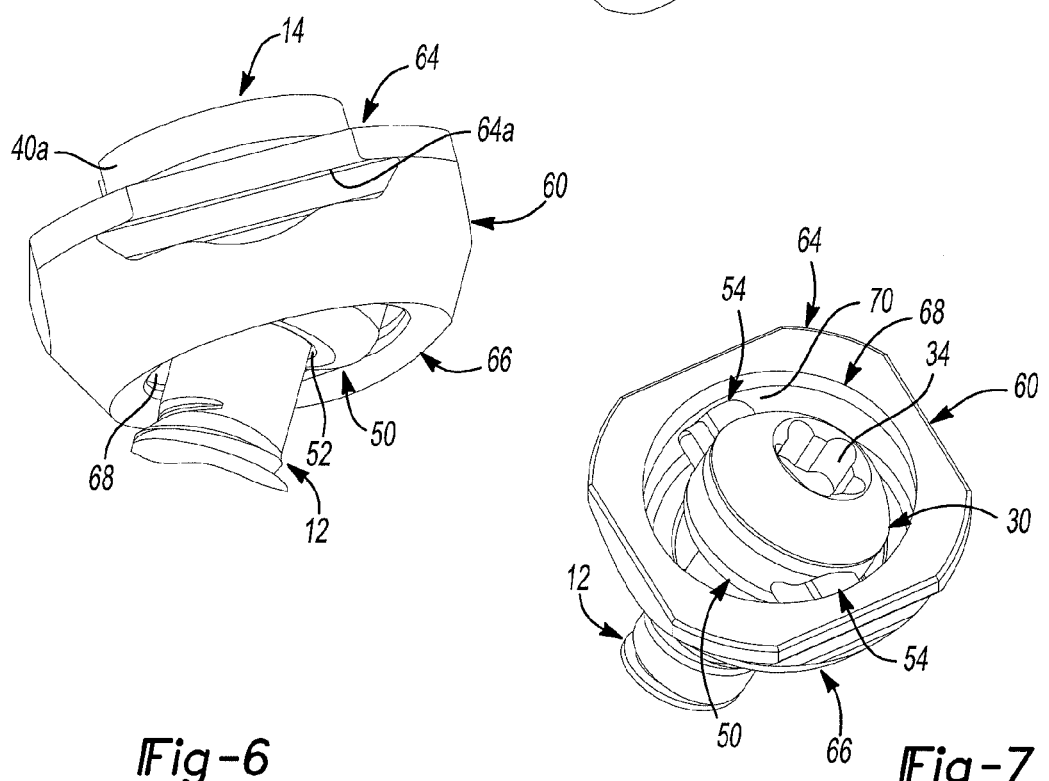
Fig-6
Fig-7

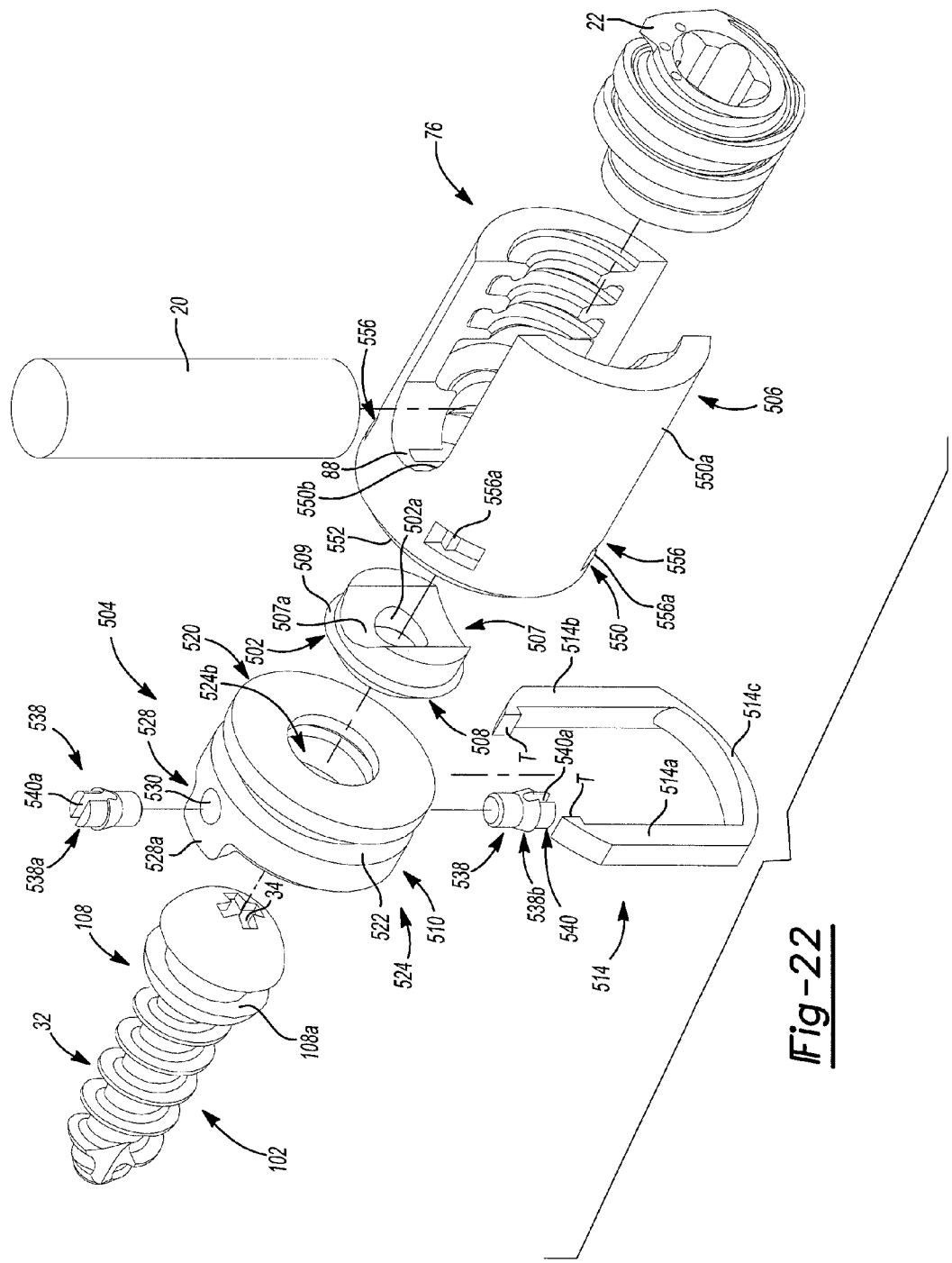

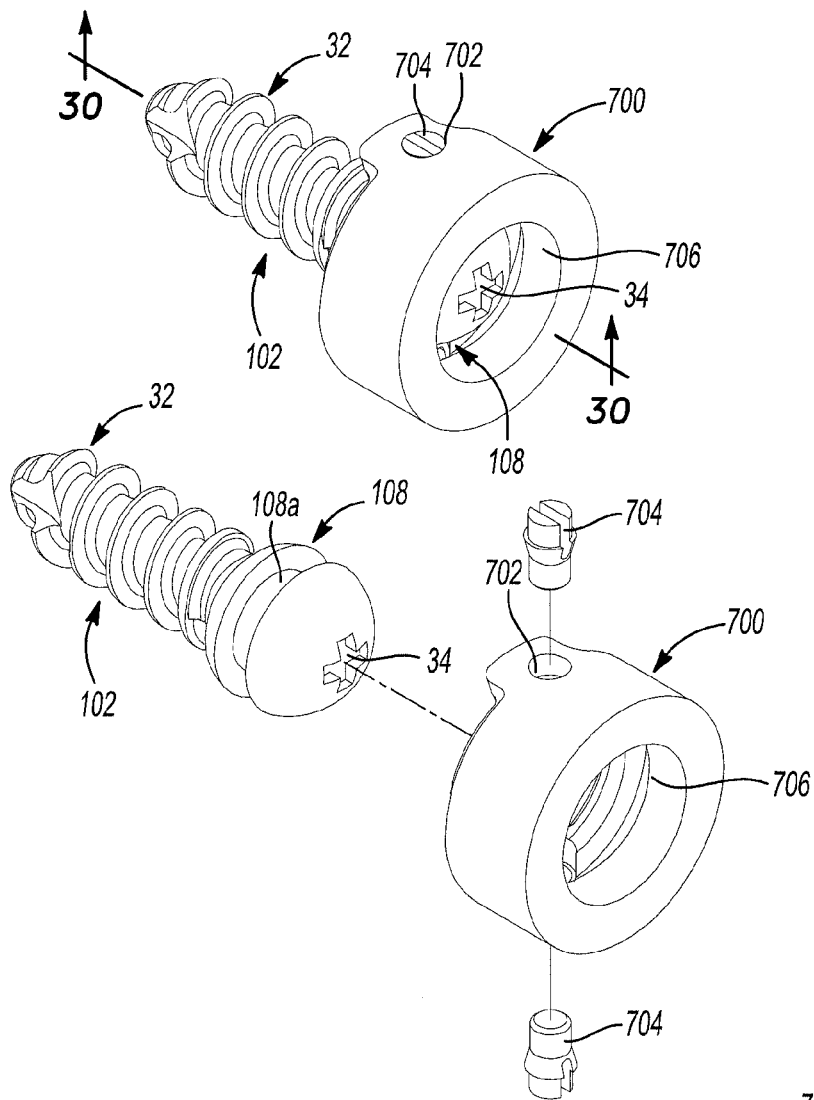
Fig-28
Fig-29
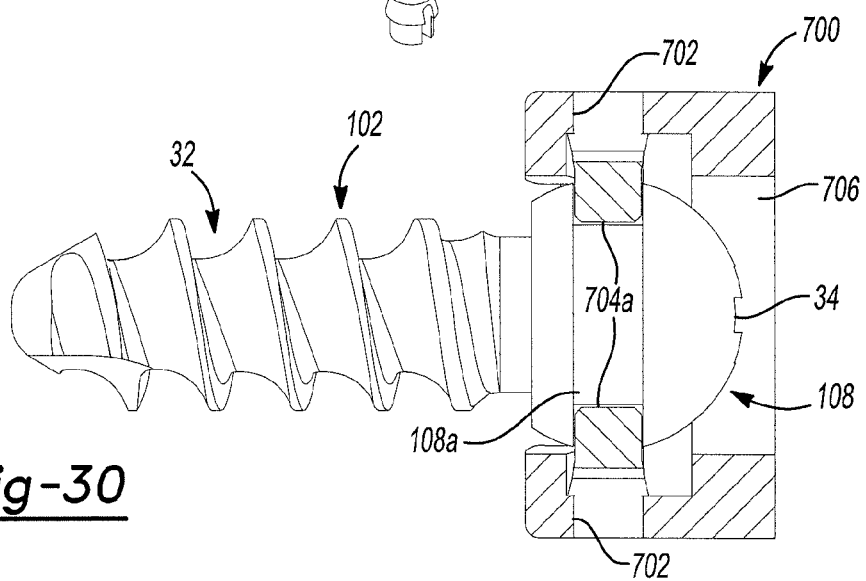
Fig-30

MULTIPLANAR BONE ANCHOR SYSTEM

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. In certain instances, it may be desirable to provide an anchor that can move relative to the connecting device. The present teachings can provide an anchor for use in repairing damaged tissue, such as a bone anchor that can be movable in multiple planes for use in a fixation procedure.

Provided is a multiplanar bone anchor system for a fixation procedure. The system can include a bone fastener. The bone fastener can include a head and a second end adapted to engage an anatomy. The bone fastener can extend along a longitudinal axis. The system can also include a coupling arrangement coupled to the head of the bone fastener so that the bone fastener is rotatable about the longitudinal axis to define a first plane of motion. The system can further include a saddle, which can be coupled to the coupling arrangement. The saddle can be movable relative to at least one of the bone fastener and the coupling arrangement to define a second plane of motion.

Further provided is a multiplanar bone anchor system for a fixation procedure. The system can include a bone fastener. The bone fastener can include a head and a second end adapted to engage an anatomy. The bone fastener can extend along a longitudinal axis. The system can also include a coupling arrangement, which can be coupled to the head of the bone fastener. The system can include a saddle. The saddle can include a first portion and a second portion. The first portion can be movable relative to the second portion along a first axis. The first axis can be transverse to the longitudinal axis of the bone fastener. The second portion can be coupled to the coupling arrangement such that the bone fastener can pivot relative to the saddle about the head of the bone fastener.

Also provided is a multiplanar bone anchor system for a fixation procedure. The system can include a bone fastener. The bone fastener can include a head and a second end adapted to engage an anatomy. The bone fastener can define a longitudinal axis. The system can also include a ring coupled about the head of the bone fastener. The ring can include at least one wing. The system can include a lock ring, which can have a distal end coupled to the head of the bone fastener. The system can further include a saddle. The saddle can include a first portion and a second portion. The first portion of the saddle can be coupled to the second portion of the saddle so as to be movable relative to the second portion. The second portion of the saddle can be coupled about the head of the bone fastener, the ring and at least a portion of the lock ring. The at least one wing of the ring can cooperate with the lock ring and the second portion of the saddle to enable the bone fastener to pivot about the head of the bone fastener. The at least one wing can also cooperate with the second portion to enable the bone fastener to rotate about the longitudinal axis.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 5 is a perspective view of an exemplary portion of the multiplanar bone anchor system of FIG. 4, which illustrates a first plane of motion;

FIG. 6 is a schematic perspective view of a second exemplary portion of the multiplanar bone anchor system of FIG. 2 moved about one of various planes of motion;

FIG. 7 is a second schematic perspective view of the second exemplary portion of the multiplanar bone anchor system of FIG. 2 moved about one of various planes of motion;

FIG. 22 is an exploded view of the multiplanar bone anchor system of FIG. 21;

FIG. 28 is a schematic perspective illustration of an exemplary assembly of a bone fastener and a multiplanar connecting system for use with a multiplanar bone anchor system according to the present teachings;

FIG. 29 is an exploded view of the assembly of FIG. 28; and

FIG. 30 is a schematic, cross-sectional illustration of the assembly of FIG. 28, taken along line 30-30 of FIG. 28.

DESCRIPTION OF VARIOUS ASPECTS

Figure 1:
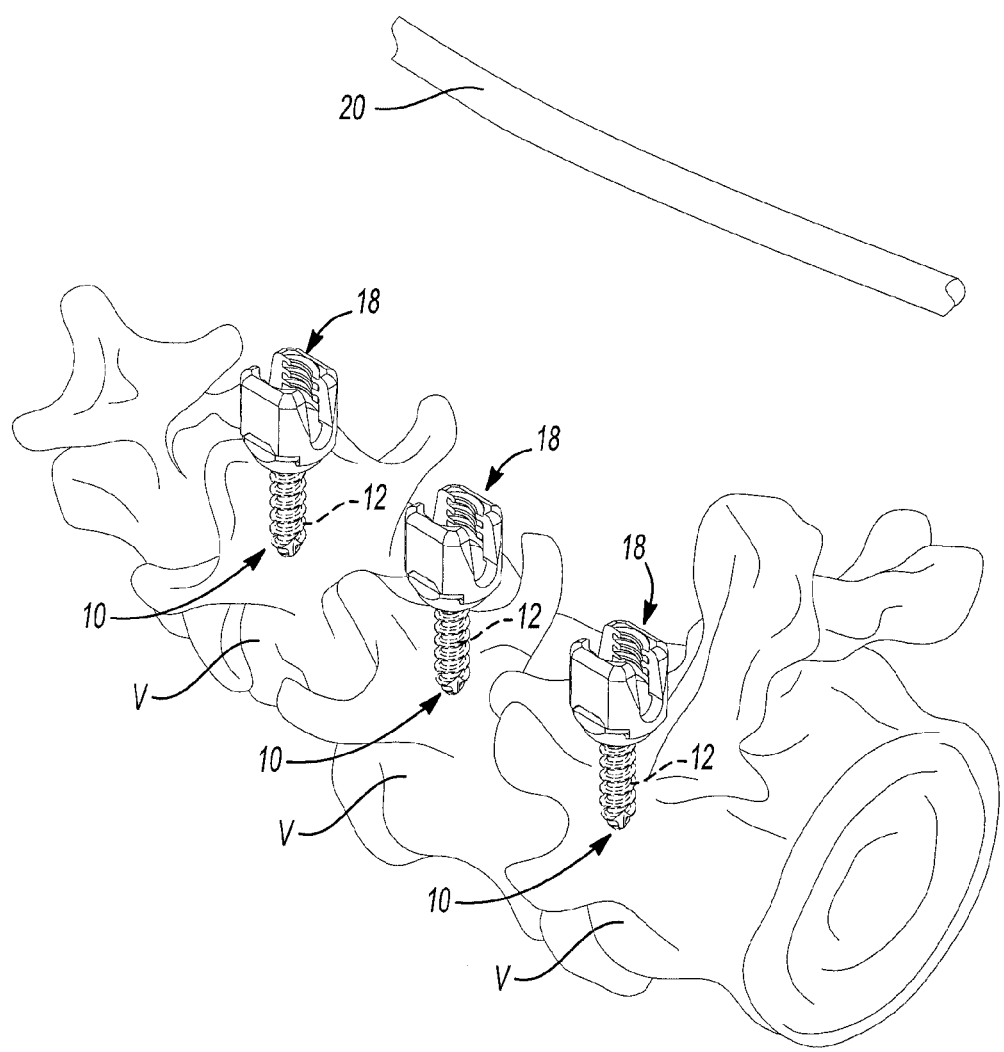
FIG. 1 is a schematic environmental illustration of an exemplary multiplanar bone anchor system for use with a connecting device in a fixation procedure according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to repair damaged tissue, such as in the case of spinal fusion, static spinal stabilization or dynamic spinal stabilization, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-8, a multiplanar bone anchor system 10 is shown. The multiplanar bone anchor system 10 may be particularly adapted for spinal fixation procedures. Various aspects of the present teachings, however, may have application for other procedures. In certain applications, the multiplanar bone anchor system 10 can be coupled to one or more vertebrae or vertebral bodies V (FIG. 1) in a posterior region of the spine. The multiplanar bone anchor system 10 can include a bone engaging member or bone fastener 12, a locking member or lock ring 14 (FIG. 3), a multiplanar coupling arrangement or system 16 (FIG. 3) and a tulip head or saddle 18.

As will be discussed in greater detail herein, the multiplanar coupling system 16 can enable the saddle 18 to move relative to the bone fastener 12 in multiple planes. Generally, the saddle 18 can be configured to receive a connecting device or rod 20, which can be used to interconnect multiple bone anchor systems 10 in an exemplary spinal fixation procedure (FIG. 1). By using the multiplanar coupling system 16, the saddle 18 can be moved relative to the bone fastener 12 in one or more planes to facilitate the connection of the connecting rod 20 to multiple bone anchor systems 10. In this regard, the vertebral bodies V of the patient may be orientated in such a manner that each bone fastener 12, when coupled to a respective vertebral body V, may be slightly offset from one another. By allowing the saddle 18 to move in multiple planes relative to the bone fastener 12, the surgeon can move the saddles 18 into alignment without regard to the placement of the bone fasteners 12. It should be noted, however, that although the multiplanar bone anchor system 10 is generally illustrated and described herein a single assembly for use with a single connecting rod 20, any combination of bone anchor systems 10 and connecting rods 20 can be employed during a surgical procedure.

For example, in a single level spinal fixation procedure, two bone anchor systems 10 can receive a single connecting rod 20. A multiple level spinal fixation procedure, however, will generally require additional bone anchor systems 10. In addition, the multiplanar bone anchor systems 10 need not be coupled to adjacent vertebral bodies V, but rather, the multiplanar bone anchor systems 10 can be positioned so as to skip adjacent vertebral bodies V, if desired.

Figure 2:
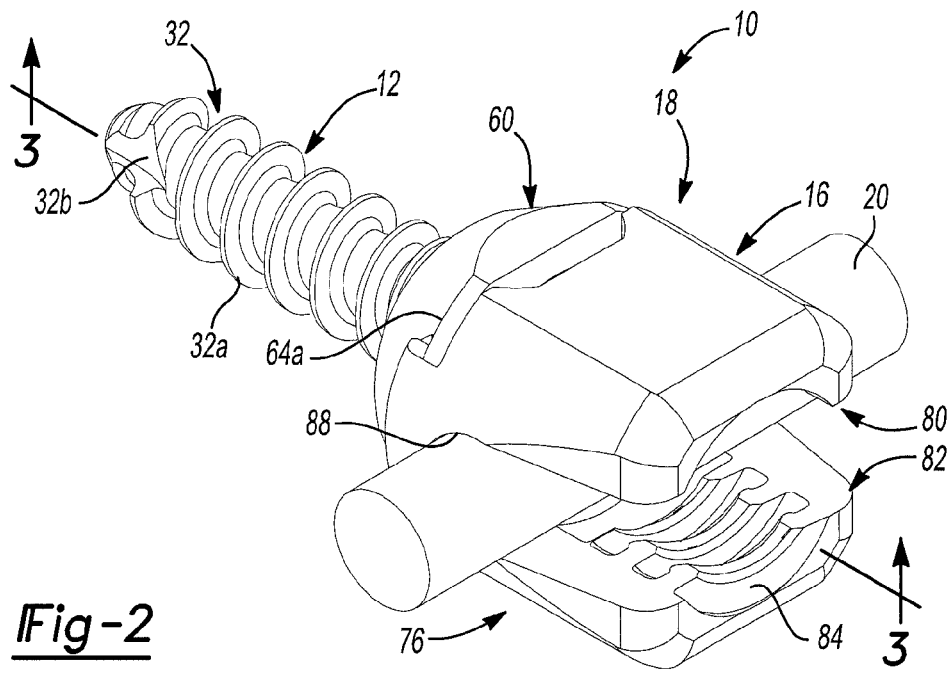
FIG. 2 is a schematic perspective illustration of the multiplanar bone anchor system of FIG. 1.
Figure 3:
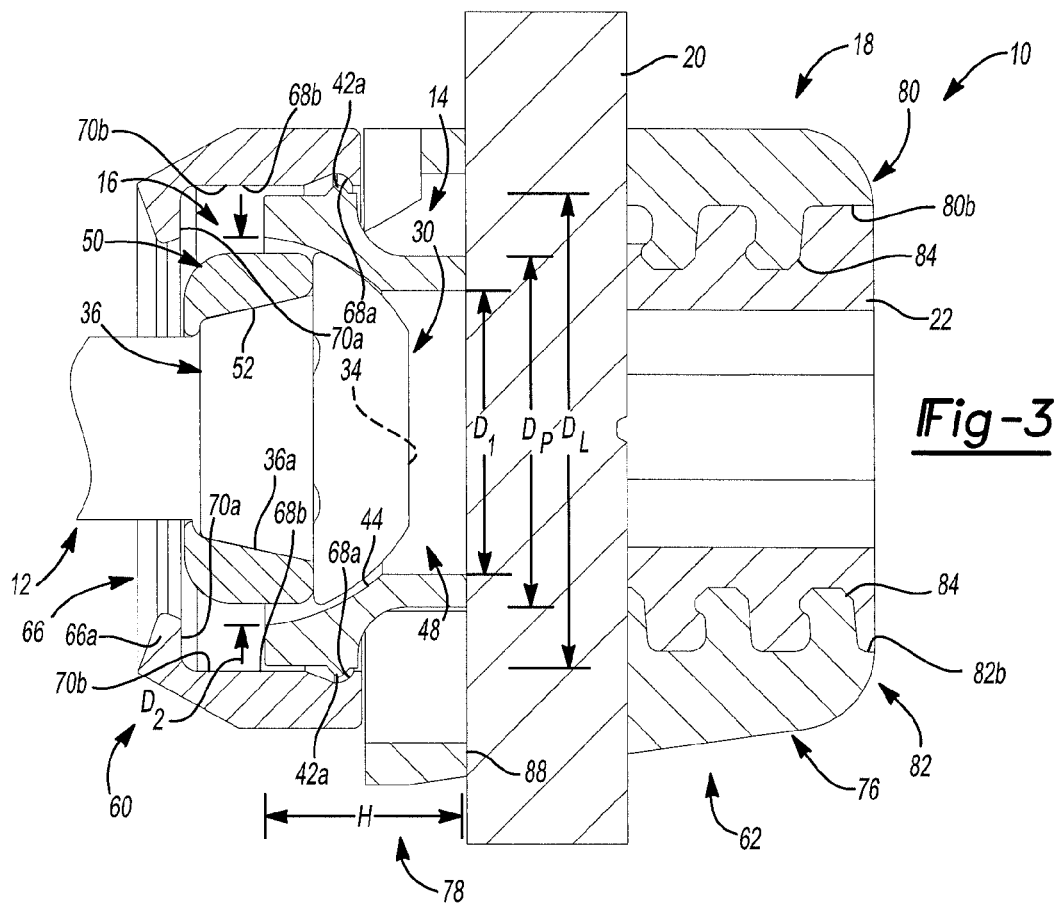
FIG. 3 is a cross-sectional view of the multiplanar bone anchor system of FIG. 2, taken along line 3-3 of FIG. 2.
Figure 4:
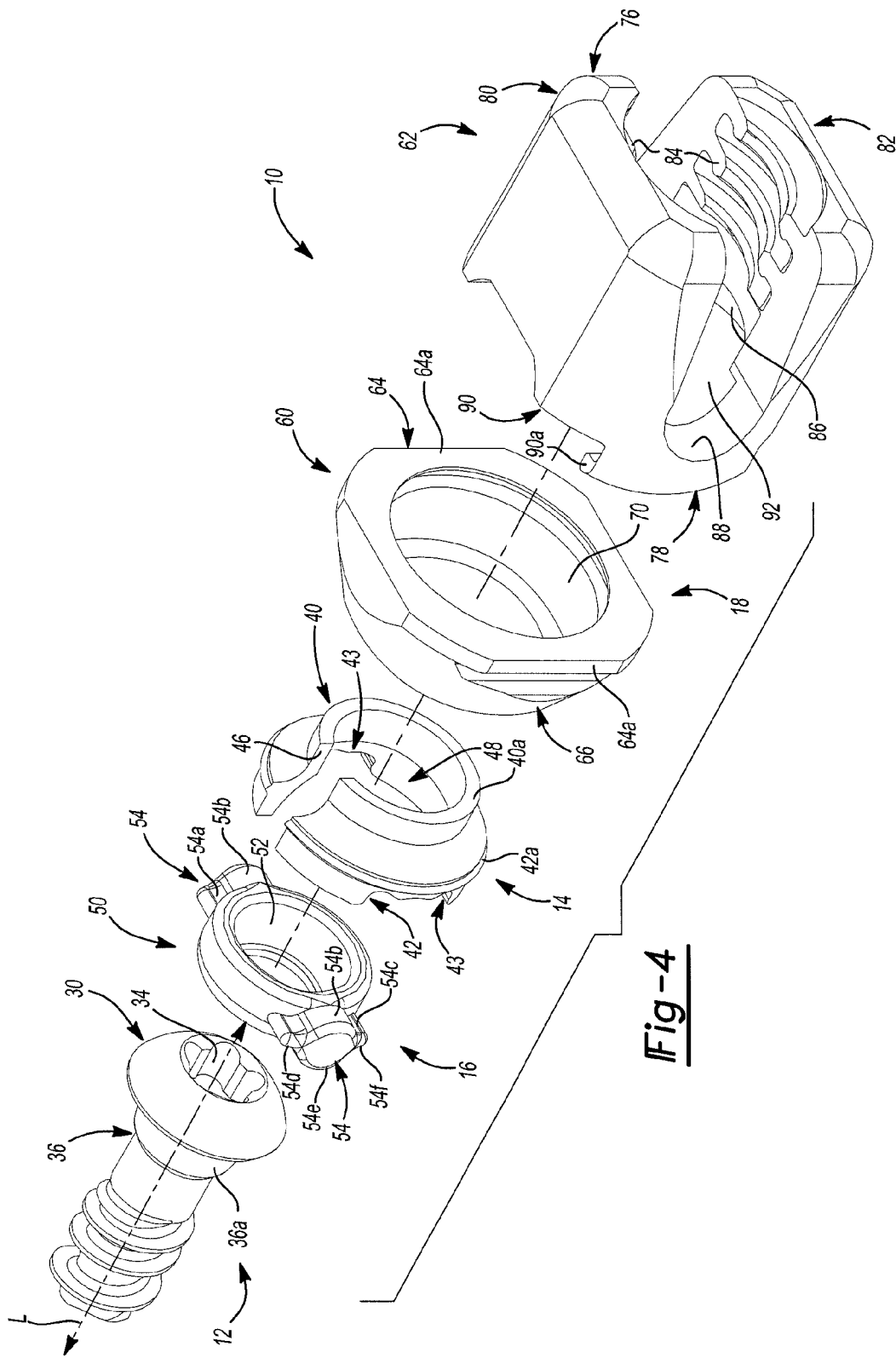
FIG. 4 is an exploded view of the multiplanar bone anchor system of FIG. 1.

With reference to FIGS. 2-4, the bone fastener 12 can be configured to engage the anatomy to couple the multiplanar bone anchor system 10 to the anatomy. The bone fastener 12 can be composed of any suitable biocompatible material, such as titanium, stainless steel, biocompatible polymers, etc. The bone fastener 12 can include a proximal end or head 30 (FIGS. 3 and 4) and a distal end or shank 32 (FIG. 2) with reference to FIGS. 3 and 4, the head 30 can be generally arcuate, and can include a driver connection feature 34 and a channel 36. The driver connection feature 34 can comprise any mating connection interface for a driver, such as a pentalobe, hexalobe, hexagon, torx, Philips, cruciate, straight, etc. Thus, the driver connection feature 34 can enable the application of a torque to drive the bone fastener 12 into the anatomy.

Briefly, it should be noted that particular tools for use with the multiplanar bone anchor system 10 are beyond the scope of the present teachings and need not be described herein. In a conventional manner insofar as the present teachings are concerned, various tools can be used to connect the multiplanar bone anchor system 10 to a respective vertebral body V. Exemplary tools can include those employed in the Polaris™ 5.5 Spinal System, commercially available from Biomet, Inc. of Warsaw, Ind., or the tools disclosed in commonly owned U.S. Patent Publication No. 2008/0077138, filed on Apr. 20, 2007 and incorporated by reference herein.

With continued reference to FIGS. 3 and 4, the channel 36 can be defined about a circumference of the head 30. The channel 36 can receive a portion of the multiplanar coupling system 16 to enable the saddle 18 to rotate about the longitudinal axis L of the bone fastener 12. Thus, the channel 36 can define a first bearing surface 36a. It should be noted that although the bone fastener 12 is illustrated and described herein as including the channel 36, the channel 36 need not be necessary to enable the saddle 18 to rotate about the longitudinal axis L of the bone fastener 12.

With reference to FIG. 2, the shank 32 of the bone fastener 12 can include a plurality of threads 32a and at least one cutting flute 32b. The at least one cutting flute 32b can cooperate with the threads 32a to cut into the anatomy, and thus, the bone fastener 12 does not require a pre-tapped hole. It should be noted that although the bone fastener 12 is illustrated and described herein as including at least one cutting flute 32b, the bone fastener 12 need not include any cutting flutes (requiring a pre-tapped hole), or could include multiple cutting flutes, if desired.

With reference to FIGS. 3 and 4, the lock ring 14 can be positioned about the head 30 of the bone fastener 12. As will be discussed herein, the lock ring 14 can lock at least one of the bone fastener 12 and the multiplanar coupling system 16 relative to the saddle 18 via a force applied by the connecting rod 20. The lock ring 14 can be generally cylindrical, and can have a height H. The height H be sized to extend above a receiver surface 88 of the saddle 18 so that coupling the connecting rod 20 to the saddle 18 can compress the lock ring 14 onto the head 30 of the bone fastener 12. With reference to FIG. 4, the lock ring 14 can include a proximal end 40, a distal end 42, a bearing surface 44, a slot 46 and a bore 48.

The proximal end 40 can include an annular projection 40a. With reference to FIG. 3, the projection 40a can have a diameter Dp, which is larger than a diameter DI of the lock ring 14. The larger diameter Dp of the projection 40a can be sized to enable the lock ring 14 to move or rotate about the head 30 of the bone fastener 12. With reference to FIGS. 3-5, the distal end 42 can include a ring or flange 42a and at least one cutout 43. The flange 42a can be formed about an exterior surface of the lock ring 14, and can retain the lock ring 14 within the saddle 18, as will be discussed in detail herein. The at least one cutout 43 can be formed along a portion of a circumference of the lock ring 14, and can be sized to cooperate with the multiplanar coupling system 16.

In one example, the lock ring 14 can include two cutouts 43, which can be positioned on opposite sides of the lock ring 14 (FIG. 4). In this example, as best illustrated in FIG. 5, the cutouts 43 can include a first curved recess 43a, a second curved recess 43b and a third curved recess 43c which can be congruent. The cutouts 43 can be generally symmetrical about a longitudinal axis of the lock ring 14. The first curved recess 43a and the third curved recess 43c can be formed from the distal end 42 to the flange 42a. The second curved recess 43b can be formed from the distal end 42 to a location adjacent to the flange 42a. In addition, the second curved recess 43b can have a radius which can be greater than a radius associated with each of the first curved recess 43a and the third curved recess 43c.

With reference to FIGS. 3 and 4, the bearing surface 44 can be formed on an interior surface of the lock ring 14. In one example, the bearing surface 44 can be formed along an interior surface of the projection 40a at the distal end 42 of the lock ring 14. The bearing surface 44 can comprise a generally concave region, which can extend from the circumference of the projection 40a. The bearing surface 44 can contact a portion of the head 30 to enable the lock ring 14 to move or articulate relative to the bone fastener 12. The bearing surface 44 can also enable the lock ring 14 to move or articulate relative to the multiplanar coupling system 16, as will be discussed herein.

With reference to FIG. 4, the lock ring 14 can also include a slot 46. The slot 46 can extend through the projection 40a, the proximal side 40 and the distal end 42. The slot 46 can enable the lock ring 14 to be coupled about the head 30 of the bone fastener 12. Note, that the slot 46 is optional, and the lock ring 14 could be continuous about the circumference of the lock ring 14.

With reference to FIG. 3, the bore 48 can be disposed about a central axis of the lock ring 14. The bore 48 can extend through the projection 40a, the proximal end 40 and the distal end 42. A first diameter D1 of the bore 48 at the projection 40a can be substantially smaller than a second diameter D2 of the bore 48 at the distal end 42 of the lock ring 14. The bearing surface 44 can be formed about the bore 48, and can transition the bore 48 from the first diameter D1 to the second diameter D2. The bore 48 can enable a driver to interface with the driver connection feature 34 formed on the head 30 of the bone fastener 12.

In one example, the multiplanar coupling system 16 can include a ring 50. The ring 50 can be disposed about a head 30 of the bone fastener 12 to enable the bone fastener 12 to move or articulate relative to the saddle 18, as shown in FIG. 3. The ring 50 can be annular, and can be sized to fit within the saddle 18 to enable the bone fastener 12 to articulate relative to the saddle 18, as shown in FIGS. 6 and 7. With reference to FIG. 4, the ring 50 can include a bore 52 and at least one wing 54. The bore 52 can be sized to enable the ring 50 to be coupled to the channel 36 of the bone fastener 12, but can also be sized so as to prevent the ring 50 from migrating above the head 30 of the bone fastener 12, as best shown in FIG. 3.

With reference to FIGS. 4 and 5, at least one wing 54 can extend outwardly from a circumference of the ring 50. In this example, the ring 50 can include two wings 54. The wings 54 can extend outwardly from opposite sides of the ring 50. The wings 54 can cooperate with the saddle 18 to enable the bone fastener 12 to move or articulate relative to the saddle 18 (FIG. 7). The wings 54 can include a first arcuate surface 54a, a second arcuate surface 54b, a third arcuate surface 54c, a fourth arcuate surface 54d, a fifth arcuate surface 54e and a sixth arcuate surface 54f. It should be noted that the shape of the wings 54 described and illustrated herein is merely exemplary, as the wings 54 could have any shape that enables the bone fastener 12 to rotate relative to the saddle 18, such as elliptical, circular, rounded square, rounded rectangular, etc.

The first arcuate surface 54a can be opposite the fourth arcuate surface 54d, the second arcuate surface 54b can be opposite the fifth arcuate surface 54e and the third arcuate surface 54c can be opposite the sixth arcuate surface 54f. Generally, the second arcuate surface 54b and the fifth arcuate surface 54e can be positioned between the first arcuate surface 54a, fourth arcuate surface 54d, third arcuate surface 54c and sixth arcuate surface 54f. The first arcuate surface 54a, second arcuate surface 54b and the third arcuate surface 54c can each contact one of the first curved recess 43a, the second curved recess 43b, third curved recess 43c, respectively, which can enable the lock ring 14 to move or articulate relative to the ring 50, as best shown in FIG. 5. The fourth arcuate surface 54d, fifth arcuate surface 54e and sixth arcuate surface 54f can cooperate with the saddle 18 to enable the bone fastener 12 to move or articulate relative to the saddle 18, as shown in FIGS. 6 and 7.

Figure 8:
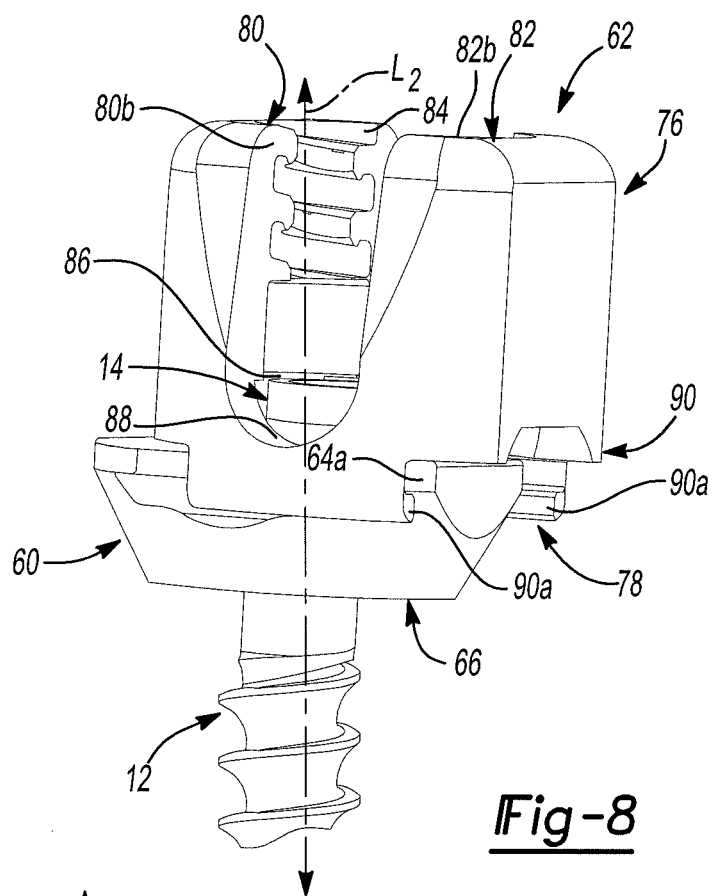
FIG. 8 is a schematic perspective view of the multiplanar bone anchor system of FIG. 2 in which a saddle associated with the multiplanar bone anchor system is moved about one of various planes of motion.

With reference to FIGS. 4 and 6-8, the saddle 18 can include a first portion or bottom portion 60 and a second portion or top portion 62. The top portion 62 can move or translate relative to the bottom portion 60 (FIG. 8). With reference to FIGS. 4 and 6-8, the bottom portion 60 can include a first or proximal end 64, a second or distal end 66, a bore 68 and a bearing surface 70. The proximal end 64 can be generally rectangular, and can include rounded corners. The proximal end 64 can be coupled to the top portion 62 (FIG. 8). The proximal end 64 can define at least one rail 64a. Generally, the top portion 62 can move or translate along the at least one rail 64*a* (FIG. 8). In one example, the proximal end 64 can define two rails 64*a*, which can be positioned on opposite sides of the bottom portion 60. As will be discussed, the diameter Dp of the lock ring 14 can define or limit the translation of the top portion 62 relative to the bottom portion 60. The proximal end 64 can taper to the distal end 66.

The distal end 66 can be adjacent to the shank 32 of the bone fastener 12, when the saddle 18 is coupled to the bone fastener 12. As best shown in FIG. 3, the distal end 66 can define a lip or stop 66*a* on an interior surface. In this example, the stop 66*a* can extend into the bore 68 of the bottom portion 60. The stop 66*a* can extend about a circumference of the bore 68, and can limit the motion or articulation of the bone fastener 12 relative to the saddle 18.

The bore 68 can be defined through the bottom portion 60. The bore 68 can be sized to receive the ring 50, the lock ring 14 and the bone fastener 12 therein. With reference to FIG. 3, the bore 68 can include bearing surface 68*a* and a sidewall 68*b*. The bearing surface 68*a* can be configured to receive the flange 42*a* of the lock ring 14, to couple the lock ring 14 to the saddle 18. In other words, the flange 42*a* of the lock ring 14 can cooperate with the bearing surface 68*a* of the bottom portion 60 to prevent the lock ring 14 from migrating out of the saddle 18. The sidewall 68*b* of the bore 68 can comprise a portion of the bearing surface 70.

The bearing surface 70 can be defined about a circumference of the bore 68. In one example, the bearing surface 70 can be formed on a portion 70*a* of the stop 66*a*, and a portion 70*b* of the sidewall 68*a* of the bore 68. The bearing surface 70 can generally be shaped so as to cooperate with the ring 50 to enable the ring 50 to move or articulate within the bottom portion 60 of the saddle 18, as best shown in FIG. 7. The relative movement between the ring 50 and the bottom portion 60 can allow the bone fastener 12 to pivot or angulate about a central axis or longitudinal axis of the bone fastener 12.

With reference to FIGS. 3, 4 and 8, the top portion 62 of the saddle 18 can be coupled to the rails 64*a* of the proximal end 64 of the bottom portion 60 so that the top portion 62 can move relative to the bottom portion 60. The top portion 62 can be substantially U-shaped and symmetrical with respect to a longitudinal axis L₂ defined by the multiplanar bone anchor system 10 (FIG. 8). The top portion 62 can include a first or proximal end 76 and a second or distal end 78. In one example, the proximal end 76 can include a first arm 80 and a second arm 82. The first arm 80 and second arm 82 can extend upwardly from the distal end 78 to define the U-shape. Each of the first arm 80 and the second arm 82 can include a mating portion 84 and a cavity 86.

The mating portion 84 can be configured to receive a fastening mechanism to couple the connecting rod 20 to the saddle 18. For example, the mating portion 84 can comprise a plurality of threads, which can be formed on an interior surface 80*b*, 82*b* of each of the first arm 80 and second arm 82. In this example, the mating portion 84 can engage threads formed on a set screw 22 to couple the connecting rod 20 to the saddle 18 (FIG. 3). It should be noted, however, that the proximal end 76 can have any suitable configuration to couple the connecting rod 20 to the saddle 18, such as keyed portions, teeth, etc.

The cavity 86 can be defined in each interior surface 80*b*, 82*b* of the first arm 80 and second arm 82. The cavity 86 can provide clearance for the movement or articulation of the top portion 62 relative to the bottom portion 60 of the saddle 18. In this regard, the cavity 86 can be defined so as to allow the top portion 62 to move over a portion of the lock ring 14, which can provide a range of motion for the top portion 62 relative to the bottom portion 60. Thus, contact between the lock ring 14 and the cavity 86 can act as a stop to limit the movement or translation of the top portion 62 relative to the bottom portion 60, however, other techniques could be used to stop or limit the movement or translation of the top portion 62 relative to the bottom portion 60

With reference to FIG. 4, the distal end 78 of the top portion 62 can be generally rectangular, and can include a first or a receiver surface 88, a second or bottom surface 90 and a central bore 92. The receiver surface 88 can receive a portion of the connecting rod 20. In one example, the receiver surface 88 can comprise a generally arcuate, concave surface that forms the U-shape of the saddle 18, however, the receiver surface 88 can comprise any desired shape, such as square, etc.

The bottom surface 90 can include at least one or more guides 90*a*. In this example, the bottom surface 90 can include two guides 90*a*. The guides 90*a* can slidably couple the top portion 62 to the bottom portion 60. In this regard, each guide 90*a* can cooperate with a respective one of the rails 44*a* to enable the top portion 62 of the saddle 18 to move or translate relative to the bottom portion 60 of the saddle 18 (FIG. 8). Generally, each guide 90*a* can comprise a C-shape, and each rail 44*a* can be received within a center of the guide 90*a*. It should be understood, however, that any suitable shape could be used to enable the top portion 62 to move or translate relative to the bottom portion 60.

The central bore 92 can be defined through the distal end 78 from the receiver surface 88 to the bottom surface 90. Generally, the central bore 92 can be sized to receive the bone fastener 12, and can cooperate with the multiplanar coupling system 16 to allow the bone fastener 12 to move in the desired planes.

With reference to FIGS. 2 and 3, the connecting rod 20 can be received within the receiver surface 88 of the saddle 18. The connecting rod 20 can be coupled to the saddle 18 via a suitable mechanical fastener, such as the set screw 22. An exemplary connecting rod 20 and set screw 22 can be substantially similar to the connecting rod and set screw employed in the Polaris™ 5.5 Spinal System, commercially available from Biomet, Inc. of Warsaw, Ind., or the connecting element disclosed in commonly owned U.S. Patent Publication No. 2008/0077138, filed on Apr. 20, 2007 and previously incorporated by reference herein. As the connecting rod 20 and the set screw 22 can be generally known, the connecting rod 20 and set screw 22 will not be discussed in great detail herein.

Briefly, however, the connecting rod 20 can comprise an elongated solid cylinder. The connecting rod 20 can also include a slight curvature, which can correspond to the natural curvature of the spine. Typically, the connecting rod 20 can be composed of a suitable biocompatible material having sufficient rigidity to fix the vertebral bodies V relative to each other. The set screw 22 can include threads, which can matingly engage the threads formed on the mating portion 84 of the proximal end 76 of the saddle 18.

With reference to FIGS. 4-8, in order to assemble the multiplanar bone anchor system 10, the ring 50 can be positioned about the channel 36 of the bone fastener 12 (FIG. 5). Then, the bottom portion 60 of the saddle 18 can be positioned about the ring 50 (FIGS. 6 and 7). The lock ring 14 can be coupled to the top portion 62. Next, the top portion 62 of the saddle 18 can be coupled to the bottom portion 60 of the saddle 18 (FIG. 8) Then, the lock ring 14 can be coupled to the head 30 of the bone fastener 12.

Once assembled, the ring 50 can cooperate with the bottom portion 60 to enable movement or rotation of the bone fastener 12 about the central or longitudinal axis of the bone fastener 12 (FIGS. 6 and 7). The lock ring 14 can cooperate with the head 30 of the bone fastener 12 to enable the bone fastener 12 to move or articulate relative to the saddle 18, about the head 30 of the bone fastener 12 (FIG. 5). The top portion 62 of the saddle 18 can cooperate with the bottom portion 60 to enable the top portion 62 of the saddle 18 to move or translate relative to the bottom portion 60 of the saddle 18 (FIG. 8). Thus, when assembled, the multiplanar bone anchor system 10 can have at least three degrees of movement or can be movable in at least three planes. By allowing the multiplanar bone anchor system 10 to move in at least three planes, the surgeon can manipulate the multiplanar bone anchor system 10 as necessary to conform to the anatomy of the patient.

With the bone fastener 12 coupled to the saddle 18 via the multiplanar coupling system 16, surgical access can be made through the skin S adjacent to the vertebral bodies V of interest (FIG. 1). The specific surgical access approaches are beyond the scope of the present application, but for example, surgical access can be obtained via a minimally invasive surgical procedure such as that used with the Polaris™ 5.5 Spinal System, commercially available from Biomet, Inc. of Warsaw, Ind., or the minimally invasive surgical procedure disclosed in commonly owned U.S. Patent Publication No. 2008/0077138, filed on Apr. 20, 2007 and previously incorporated by reference herein.

Next, one or more multiplanar bone anchor systems 10 can be coupled to a respective vertebral body V via the bone fastener 12 (FIG. 1). Various techniques can be used to couple the multiplanar bone anchor systems 10 to the anatomy, such as those described in commonly owned U.S. Patent Publication No. 2008/0077138, filed on Apr. 20, 2007, previously incorporated by reference herein. In one example, if each bone fastener 12 includes the driver connection feature 34 defined in the head 30, a suitable tool can be coupled to the driver connection feature 34 to drive the bone fastener 12 into the anatomy in a conventional manner. Once the multiplanar bone anchor systems 10 are coupled to the anatomy, the connecting rod 20 can be inserted into the saddle 18 of each of the multiplanar bone anchor systems 10. Generally, the connecting rod 20 can be inserted such that the connecting rod 20 rests on the receiver surface 88 of the distal end 78 of the saddle 18 (FIG. 2).

With the connecting rod 20 positioned in the saddles 18 of the multiplanar bone anchor systems 10, the set screw 22 can be coupled to each mating portion 68 of each saddle 18 (FIG. 3). The coupling of the set screw 22 can apply a force to the lock ring 14 to fixedly couple or lock the angular position of the bone fastener 12 relative to the saddle 18. In this regard, the lock ring 14 can apply a force to the head 30 of the bone fastener 12, which in turn, can provide a force on the ring 50. Additionally, the lock ring 14 can apply a force directly to the ring 50. The force on the ring 50, can in turn be applied to the bottom portion 60 of the saddle 18 to thereby fix the position of the bone fastener 12 relative to the saddle 18.

Figure 9:
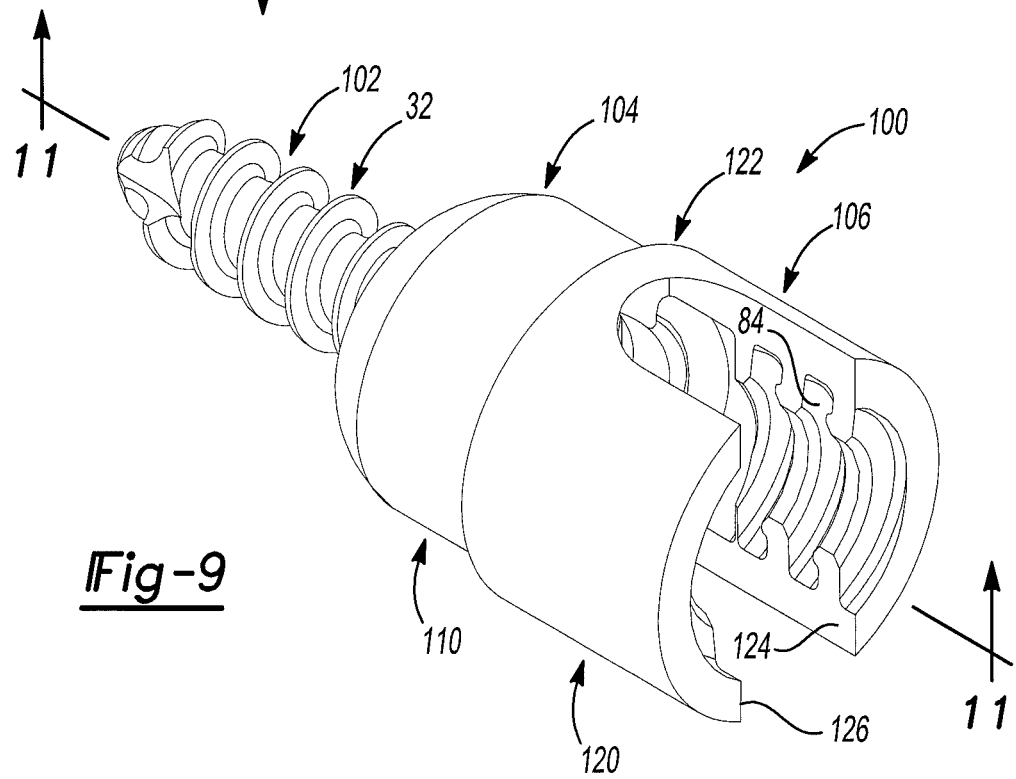
FIG. 9 is a schematic perspective illustration of another exemplary multiplanar bone anchor system for use with a connecting device in a fixation procedure according to the present teachings.
Figure 10:
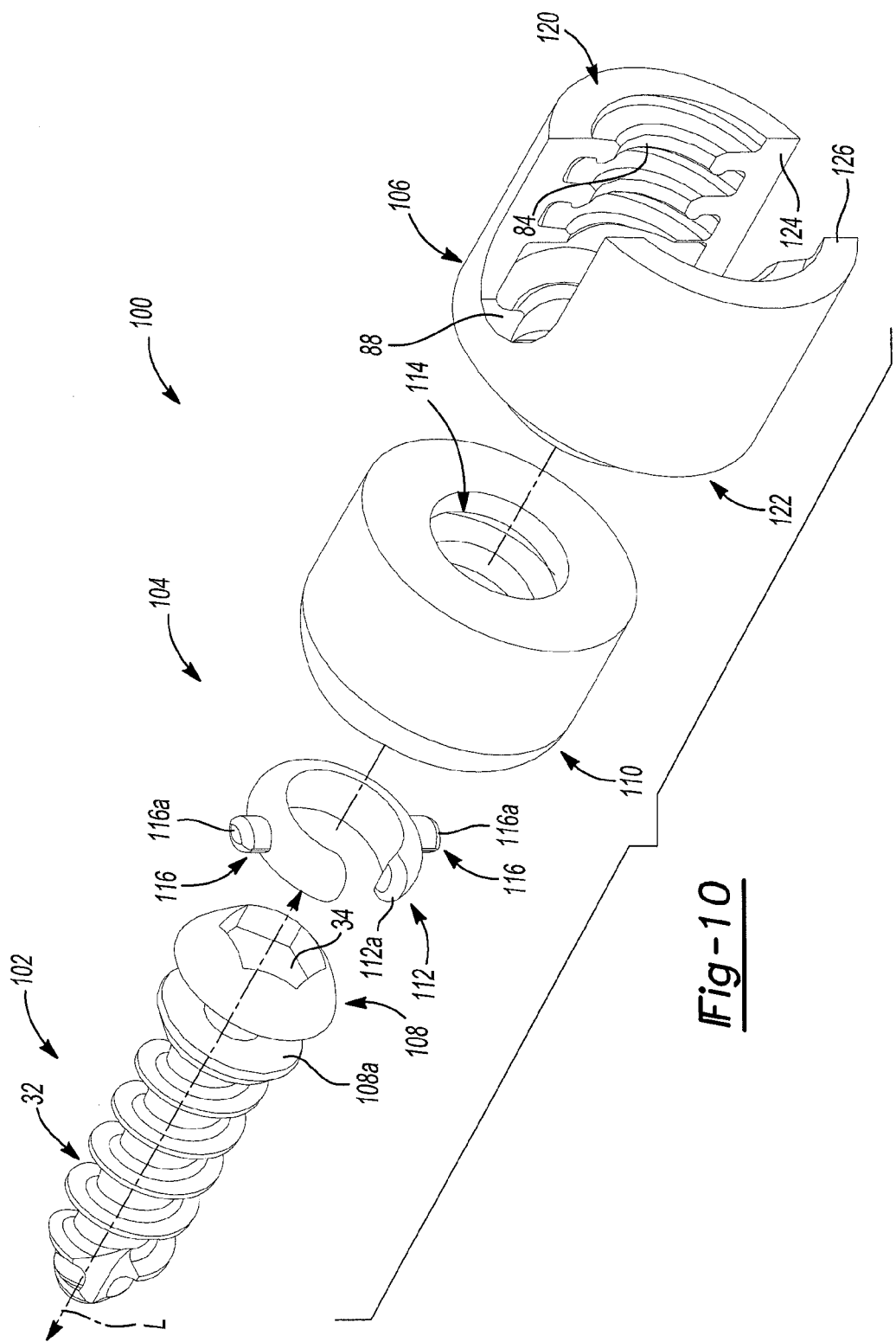
FIG. 10 is an exploded view of the multiplanar bone anchor system of FIG. 9.
Figure 11:
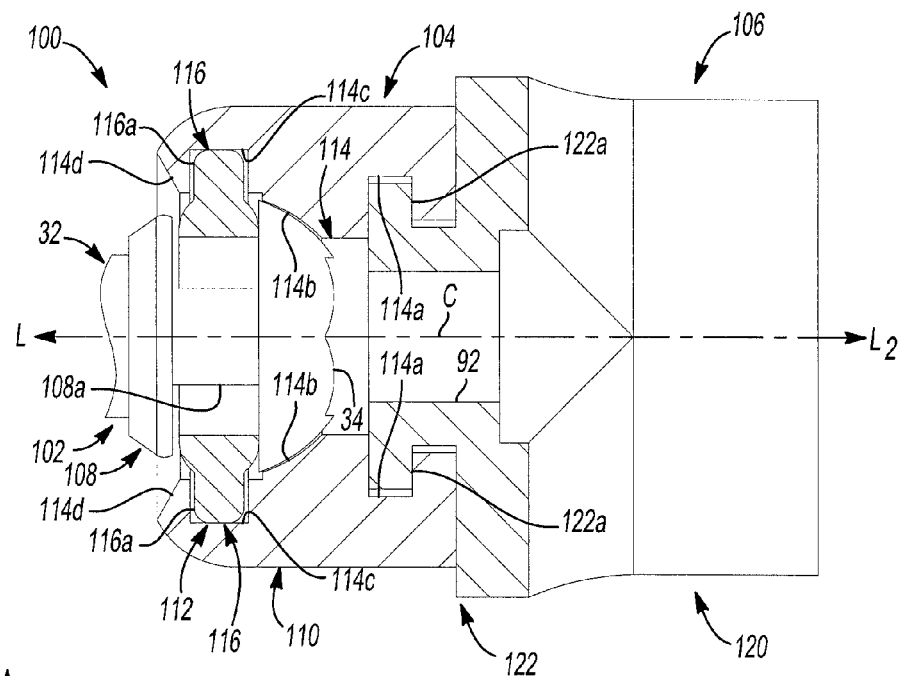
FIG. 11 is a schematic, cross-sectional illustration of the multiplanar bone anchor system of FIG. 9, taken along line 11-11 of FIG. 9.

With reference now to FIGS. 9-11, in one example, a multiplanar bone anchor system 100 can be employed with the connecting rod 20 to repair a damaged portion of an anatomy. As the multiplanar bone anchor system 100 can be similar to the multiplanar bone anchor system 10 described with reference to FIGS. 1-8, only the differences between the multiplanar bone anchor system 10 and the multiplanar bone anchor system 100 will be discussed in great detail herein, and the same reference numerals will be used to denote the same or similar components. The multiplanar bone anchor system 100 can include a bone fastener 102, a multiplanar coupling arrangement or system 104 and a saddle 106. It should be noted, that although the multiplanar bone anchor system 100 is described and illustrated herein as not including a lock ring 14, a suitable lock ring 14 could be employed with the multiplanar bone anchor system 100, if desired.

With continued reference to FIGS. 9-11, the bone fastener 102 can be configured to engage the anatomy to couple the multiplanar bone anchor system 100 to the anatomy. The bone fastener 102 can be composed of any suitable biocompatible material, such as titanium, stainless steel, biocompatible polymers, etc. The bone fastener 102 can include a head 108 and the shank 32. The head 108 can be generally arcuate, and can include the driver connection feature 34 and a channel 108a.

The channel 108a can be defined about a circumference of the head 108, generally between the head 108 and the shank 32. The channel 108a can receive a portion of the multiplanar coupling system 104 to enable the saddle 106 to rotate about the longitudinal axis L of the bone fastener 102 (FIG. 10). Thus, the channel 108a can define a first bearing surface. It should be noted that although the bone fastener 102 is illustrated and described herein as including the channel 108a, the channel 108a need not be necessary to enable the saddle 106 to rotate about the longitudinal axis L of the bone fastener 102.

In one example, with continued reference to FIGS. 9-11, the multiplanar coupling system 104 can include a connecting arm 110 and a bearing member or ring 112. The connecting arm 110 and the ring 112 can cooperate with the bone fastener 102 to enable the bone fastener 102 to move relative to the saddle 106. The connecting arm 110 can be disposed about a head 108 of the bone fastener 102 to enable the bone fastener 102 to move or articulate relative to the saddle 106 as shown in FIG. 11. In this example, the connecting arm 110 can be annular, and can be coupled to the saddle 106. The connecting arm 110 can include a bore 114. The bore 114 can be formed about a central axis C of the connecting arm 110. As best shown in FIG. 11, the bore 114 can include a mating portion 114a, a recess 114b, a coupling portion 114c and a tapered portion 114d.

The mating portion 114a can couple the connecting arm 110 to the saddle 106. It should be noted that the mating portion 114a can be configured so that the saddle 106 can move or translate relative to the connecting arm 110. For example, the mating portion 114a can comprise opposing guides or slots formed through a portion of the connecting arm 110 that can slidably receive a portion of the saddle 106. It should be noted, however, any suitable method or configuration can be used to slidably couple the saddle 106 to the connecting arm 110, such as a dovetail, rails, etc.

The recess 114b can be defined between the mating portion 114a and the at least one coupling portion 114c. Generally, the recess 114b can be arcuate, and in one example, can be hemispherical. The recess 114b can provide at least clearance for the rotation of the head 108 of the bone fastener 102 within and relative to the connecting arm 110. In this regard, the recess 118 can be sized to enable at least rotation about the longitudinal axis L of the bone fastener 102, and can also be sized to enable rotation of the connecting arm 110 relative to the head 108 of the bone fastener 102, if desired.

The coupling portion 114c can be defined between the recess 114b and the tapered portion 114d. In one example, the coupling portion 114c can comprise a channel defined about the circumference of the connecting arm 110. Generally, the coupling portion 114c can be configured to receive the ring 112, which can movably or rotatably couple the bone fastener 102 to the connecting arm 110, as will be discussed herein.

The tapered portion 114d can be defined at a distalmost end of the bore 114. The tapered portion 114d can provide clearance for the angular movement of the bone fastener 102 relative to the saddle 106. In this regard, the tapered portion 114d can be formed about a circumference of the bore 114, and the shank 32 of the bone fastener 102 can contact the tapered portion 114d to limit the angular motion of the bone fastener relative to the connecting arm 110. Thus, the tapered portion 114d can provide a stop or limit for the angular movement of the bone fastener 102 relative to the saddle 106.

With reference to FIGS. 10 and 11, the ring 112 can be coupled to the channel 108a of the head 108 of the bone fastener 102, and can cooperate with the bore 114 to enable the bone fastener 102 to move or rotate relative to the connecting arm 110. In one example, the ring 112 can comprise a generally C-shape body, and can have a slot 112a. The ring 112 can be at least partially received within the channel 108a of the head 108. Generally, the ring 112 can be snap-fit into the channel 108a of the bone fastener 102. In one example, the ring 112 can have an inner diameter which can be greater than an outer diameter of the channel 108a of the head 108 to prevent separation of the ring 112 from about the head 108 of the bone fastener 102. It should be noted, however, that the ring 112 could have a continuous annular body, such as an O-shape, and in this case, the ring 112 could be threaded over the shank 32 into the channel 36.

With reference to FIG. 10, the ring 112 can include at least one wing 116. The at least one wing 116 can extend outward from the body of the ring 112 to engage the coupling portion 114c of the bore 114. In this example, the ring 112 can include two wings 116, which can each be received within and slidably coupled to the coupling portion 114c of the bore 114 of the connecting arm 110. The wings 116 can comprise bearing surfaces, which can cooperate with the coupling portion 114c to enable the rotation of the bone fastener 102 about the connecting arm 110. Thus, the wings 116 can have any shape, which can enable the wings 116 to move or slide within the coupling portion 114c of the bore 114, such as elliptical, spherical, rounded, annular, rounded square, rounded rectangular, etc. The wings 116 can also include at least one tapered surface 116a, which can enable the connecting arm 110 to move or pivot relative to the bone fastener 102. In this example, the wings 116 can include two opposed tapered surfaces 116a, which can cooperate with the coupling portion 114c to enable the connecting arm 110 to move or pivot about the head 108 of the bone fastener 102.

With reference to FIGS. 9-11, the saddle 106 can be coupled to the multiplanar coupling system 104 via the connecting arm 110. Generally, the saddle 106 can be coupled to the connecting arm 110 so that the saddle 106 can move or translate relative to the multiplanar coupling system 106 and the bone fastener 102. The saddle 106 can be substantially U-shaped and symmetrical with respect to a longitudinal axis L defined by the multiplanar bone anchor system 100. In one example, the saddle 106 can include a first or proximal end 120 and a second or distal end 122. In one example, the proximal end 120 can include a first arm 124 and a second arm 126. The first arm 124 and second arm 126 can extend upwardly from the distal end 122 to define the U-shape. Each of the first arm 124 and the second arm 126 can include the mating portion 84.

With reference to FIGS. 10 and 11, the distal end 122 can be generally rectangular, and can include the receiver surface 88 (FIG. 10), at least one rail 122a (FIG. 11) and the central bore 92 (FIG. 11). In one example, the distal end 122 can include two rails 122a. Generally, the rails 122a can be formed on opposite sides of the bore 92, and can extend outwardly from the bore 92. The rails 122a can slidably couple the saddle 106 to the connecting arm 110. In this regard, each rail 122a can cooperate with a respective one of the guides or slots of the mating portion 114a to enable the saddle 106 to move or translate relative to the connecting arm 110 and bone fastener 102. It should be understood, however, that any suitable mechanism could be used to enable the saddle 106 to move or translate relative to the connecting arm 110, such as a dovetail assembly, etc. Further, the distal end 122 could include only one rail 122a, if desired. It should also be understood that the saddle 106 could include the mating portion 114a and the rails 122a could be formed on the connecting arm 110 to enable the relative motion between the saddle 106 and the connecting arm 110, if desired.

With reference to FIGS. 10 and 11, in order to assemble the multiplanar bone anchor system 100, the ring 112 can be coupled to the channel 108a of the bone fastener 102. Then, the connecting arm 110 can be coupled to the ring 112 such that the wings 116 of the ring 112 are received within the coupling portion 114c of the connecting arm 110. The saddle 106 can be positioned so that the rails 122a are slidably coupled to the mating portion 114a of the connecting arm 110.

Once assembled, the connecting arm 110 can cooperate with the ring 112 to enable movement or rotation of the bone fastener 102 about the central or longitudinal axis of the bone fastener 102, which provides a first plane of motion. In addition, the tapered surfaces 116a of the wings 116 can cooperate with the coupling portion 114c of the connecting arm 110 to enable the connecting arm 110 to move or pivot relative to the bone fastener 102, about the head 108 of the bone fastener 102, thereby providing a second plane of motion. The saddle 106 can also cooperate with the connecting arm 110 to enable the saddle 106 to move or translate relative to the connecting arm 110, which can provide a third plane of motion. Thus, when assembled, the multiplanar bone anchor system 100 can have at least three planes or degrees of motion. By allowing the multiplanar bone anchor system 100 to move in at least three planes, the surgeon can manipulate the multiplanar bone anchor system 100 as necessary to conform to the anatomy of the patient.

As the surgical insertion and use of the multiplanar bone anchor system 100 in a fixation procedure can be similar to the surgical insertion and insertion of the multiplanar bone anchor system 10 in a fixation procedure, the surgical insertion and use of the multiplanar bone anchor system 100 will not be discussed in great detail herein. Briefly, however, once the multiplanar bone anchor system 100 is secured to the anatomy, the multiplanar coupling system 104 and the saddle 106 can be moved, pivoted or rotated relative to the bone fastener 102 into the desired alignment for the fixation procedure. Once the aligned, the connecting rod 20 can be coupled to a desired number of multiplanar bone anchor systems 100.

Figure 12:
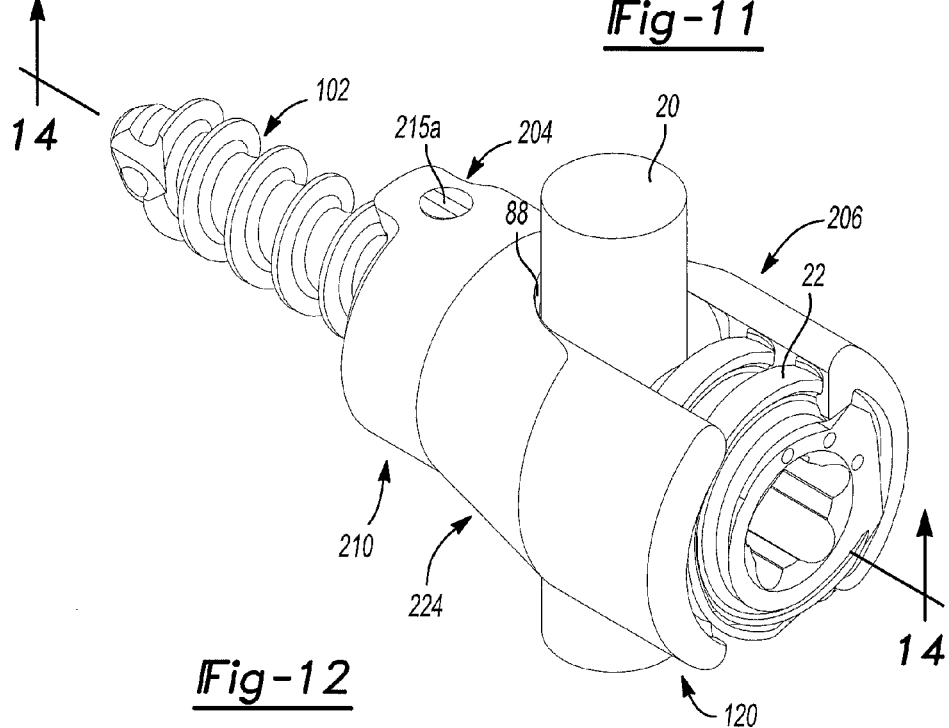
FIG. 12 is a schematic perspective illustration of another exemplary multiplanar bone anchor system for use with a connecting device in a fixation procedure according to the present teachings.
Figure 13:
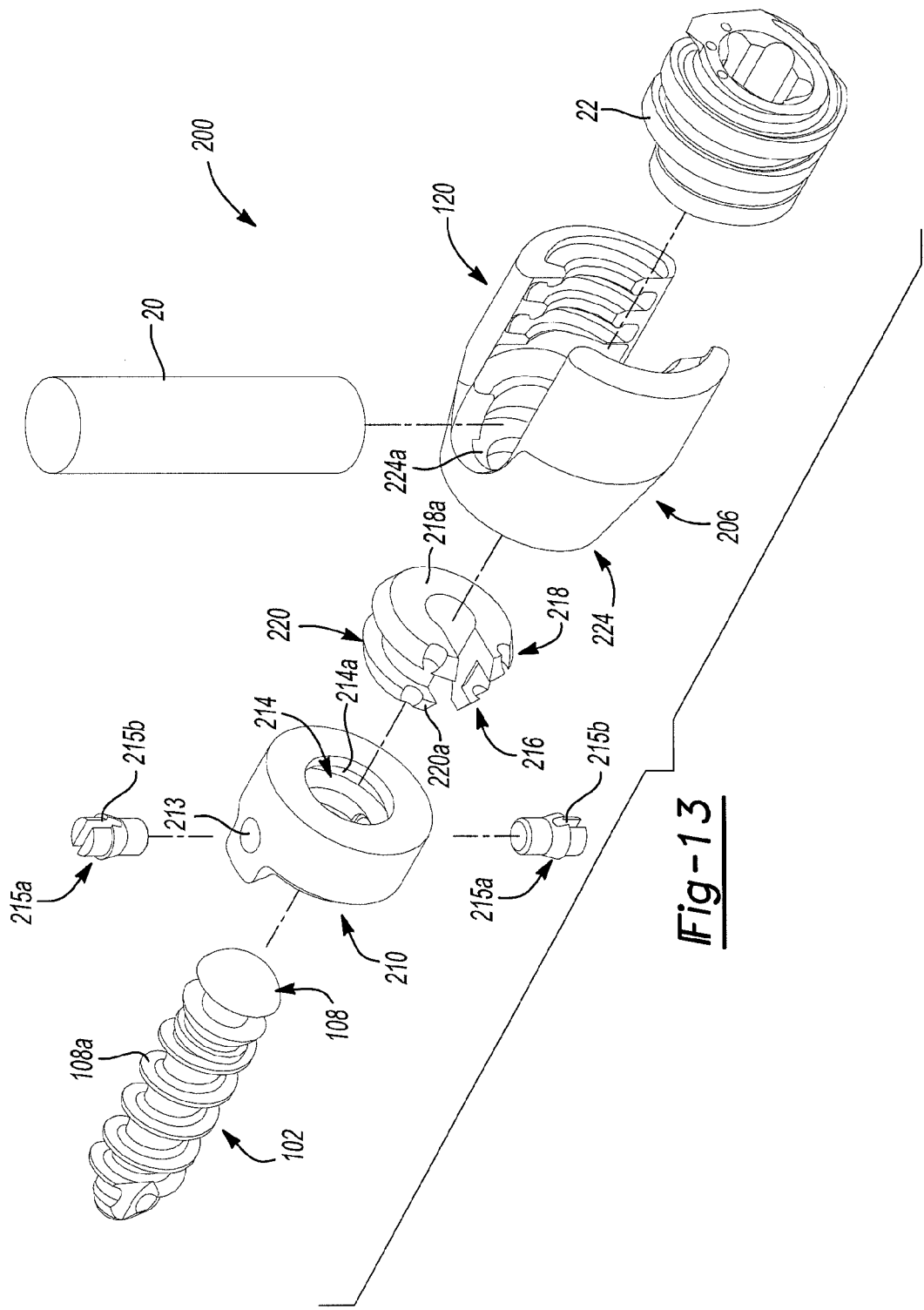
FIG. 13 is an exploded view of the multiplanar bone anchor system of FIG. 12.
Figure 14:
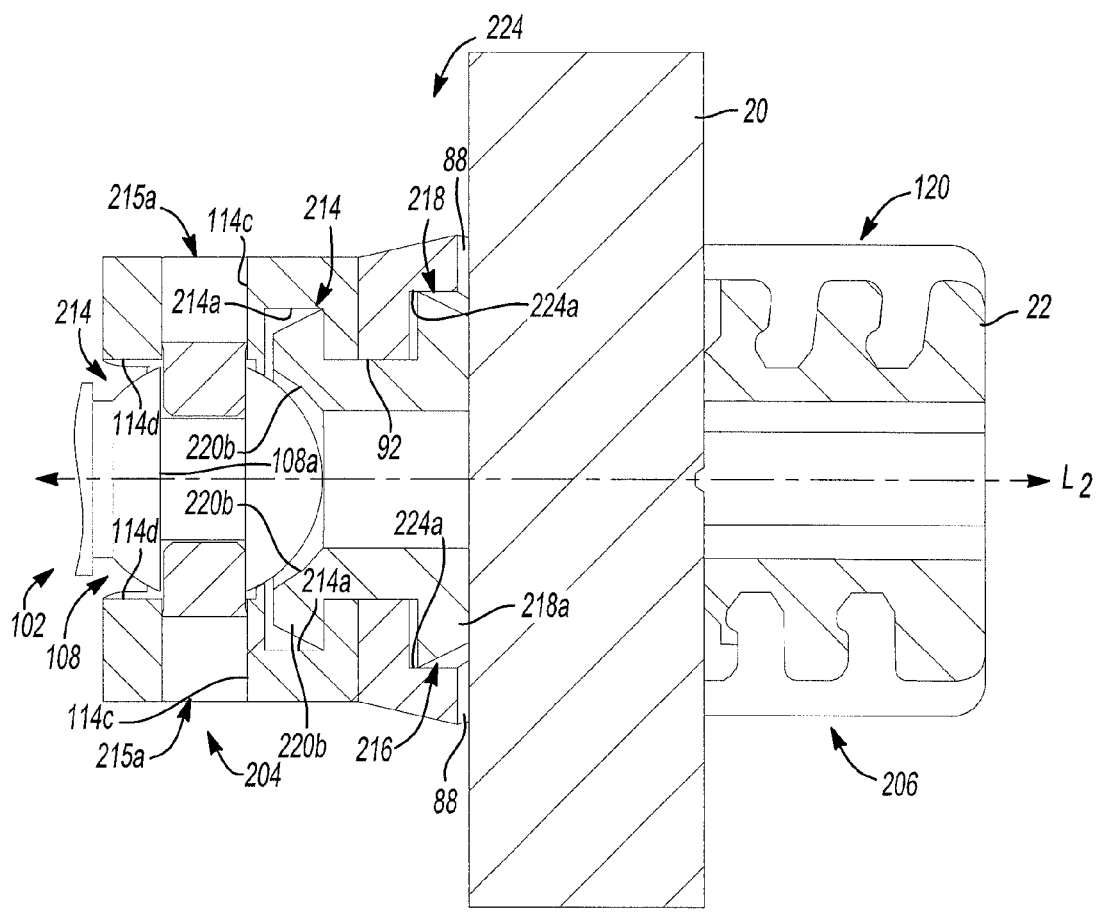
FIG. 14 is a schematic, cross-sectional illustration of the multiplanar bone anchor system of FIG. 12, taken along line 14-14 of FIG. 12.

With reference now to FIGS. 12-14, in one example, a multiplanar bone anchor system 200 can be employed with the connecting rod 20 to repair a damaged portion of an anatomy. As the multiplanar bone anchor system 200 can be similar to the multiplanar bone anchor system 100 described with reference to FIGS. 9-11, only the differences between the multiplanar bone anchor system 100 and the multiplanar bone anchor system 200 will be discussed in great detail herein, and the same reference numerals will be used to denote the same or similar components. The multiplanar bone anchor system 200 can include the bone fastener 102, a multiplanar coupling arrangement or system 204 and a saddle 206.

With reference to FIGS. 12-14, the multiplanar coupling system 204 can include a connecting arm 210, at least one plug 215 and a retaining ring 216. The connecting arm 210 can cooperate with the bone fastener 102 to enable the bone fastener 102 to move relative to the saddle 206. The connecting arm 210 can be disposed about a head 108 of the bone fastener 102 to enable the bone fastener 102 to move or articulate relative to the saddle 206. In this example, the connecting arm 210 can be annular, and can be coupled to the saddle 206. The connecting arm 210 can include at least one coupling feature 213 and a bore 214. The at least one coupling feature 213 can couple the ring 215 to the connecting arm 210, and in one example, the at least one coupling feature 213 can comprise two coupling features 213. In this example, the coupling features 213 can comprise bores, which can be defined through opposite sides of the connecting arm 210 to the bore 214. The bore 214 can be formed about a central axis C of the connecting arm 210. As best shown in FIG. 14, the bore 214 can include a mating portion 214a, the coupling portion 114c and the tapered portion 114d.

The mating portion 214a can cooperate with the retaining ring 216 to couple the connecting arm 210 to the saddle 206. Generally, the mating portion 214a can be configured so that the saddle 206 can move relative to the connecting arm about via the retaining ring 216. In this example, the mating portion 214a can comprise opposing guides or slots formed through a portion of the connecting arm 210, which can slidably receive a portion of the retaining ring 216. It should be noted, however, any suitable method or configuration can be used to movably couple the saddle 206 to the connecting arm 210, such as a dovetail, rails, etc.

With reference to FIG. 13, in one example, the at least one plug 215a can comprise two plugs 215a. The plugs 215a can engage the coupling portion 114c of the bore 214. In this example, each of the plugs 215a can be received within and slidably coupled to the coupling portion 114c of the bore 214 of the connecting arm 210. The plugs 215a can comprise bearing surfaces, which can cooperate with the coupling portion 114c to enable the rotation of the bone fastener 102 about the connecting arm 210. Thus, the plugs 215a can have any shape, which can enable the plugs 215a to move or slide within the coupling portion 114c of the bore 114, such as elliptical, spherical, rounded, annular, rounded square, rounded rectangular, etc. In one example, the plugs 215a can each include a cut out (or similar features) 215b, which can enable the plugs 215a to be snap-fit or press-fit into the connecting arm 210. It should be understood, however, that the plugs 215a could be integrally formed with the connecting arm 210, if desired. The plugs 215a can cooperate with the coupling portion 114c to enable the connecting arm 210 to move or pivot about the head 108 of the bone fastener 102.

As best shown in FIG. 14, the retaining ring 216 can couple the saddle 206 to the connecting arm 210. In this regard, the retaining ring 216 can include a first or proximal end 218 and a second or distal end 220. The proximal end 218 can be coupled to a portion of the saddle 206, as will be discussed, and the distal end 220 can be coupled to the mating portion 214a of the connecting arm 210. The retaining ring 216 can comprise any suitable structure, such as an annular ring, which may or may not include a continuous, uninterrupted circumference. In this example, the retaining ring 216 can comprise a C-shaped ring, however, it should be understood that the retaining ring 216 could also comprise a non-annular structure, such as a rectangular structure, square structure, etc.

The proximal end 218 of the retaining ring 216 can include a projection 218a, which can couple the proximal end 218 to the saddle 206. The distal end 220 can also include a projection 220a, which can couple the distal end 220 to the mating portion 214a. The projection 220a of the distal end 220 can also include a recess 220b, as best shown in FIG. 14. The recess 220b can allow the head 108 of the bone fastener 102 to rotate about the connecting arm 210 without contacting the retaining ring 216.

The saddle 206 can be coupled to the connecting arm 210 via the retaining ring 216. Generally, the saddle 206 can be coupled to the connecting arm 210 so that the saddle 206 can move or rotate relative to the multiplanar coupling system 206 and the bone fastener 102. The saddle 206 can be substantially U-shaped and symmetrical with respect to a longitudinal axis L defined by the multiplanar bone anchor system 200 (FIG. 14). In one example, the saddle 206 can include the first or proximal end 120 and a second or distal end 224.

With reference to FIG. 14, the distal end 224 can be generally annular, and can include the receiver surface 88, at least one channel 224a and the central bore 92. In this example, the distal end 224 can include two channels 224a. Generally, the channels 224a can be formed on opposite sides of the bore 92. The channels 224a can couple the saddle 206 to the connecting arm 210. In this regard, the channels 224a can receive the projection 220a of the distal end 220 of the retaining ring 216 to couple the saddle 206 to the connecting arm 210 and bone fastener 102.

With reference to FIGS. 13 and 14, in order to assemble the multiplanar bone anchor system 200, the retaining ring 216 can be coupled to the channels 224a of the saddle 206. With the retaining ring 216 coupled to the saddle 206, the distal end 220 of the retaining ring 216 can be pushed into the connecting arm 210, such that the projection 220a of the retaining ring 216 fits within the mating portion 214a of the connecting arm 210. Then, the connecting arm 210 can be positioned over the bone fastener 102, and the plugs 215a can be coupled to the connecting arm 210 so that the plugs 215a are received through the coupling features 213 of the connecting arm 210.

Once assembled, the connecting arm 210 can cooperate with the plugs 215a to enable movement or rotation of the bone fastener 102 about the central or longitudinal axis of the bone fastener 102, which provides a first plane of motion. In addition, the plugs 215a can cooperate with the coupling portion 114c of the connecting arm 210 to enable the connecting arm 210 to move or pivot relative to the bone fastener 102, about the head 108 of the bone fastener 102, thereby providing a second plane of motion. The saddle 206 can also cooperate with the connecting arm 210 via the retaining ring 216 to enable the saddle 206 to move or rotate relative to the connecting arm 210, which can provide a third plane of motion. Thus, when assembled, the multiplanar bone anchor system 200 can have at least three planes or degrees of motion. By allowing the multiplanar bone anchor system 200 to move in at least three planes, the surgeon can manipulate the multiplanar bone anchor system 200 as necessary to conform to the anatomy of the patient.

As the surgical insertion and use of the multiplanar bone anchor system 200 in a fixation procedure can be similar to the surgical insertion and insertion of the multiplanar bone anchor system 100 in a fixation procedure, the surgical insertion and use of the multiplanar bone anchor system 200 will not be discussed in great detail herein. Briefly, however, once the multiplanar bone anchor system 200 is secured to the anatomy, the multiplanar coupling system 204 and the saddle 206 can be moved, pivoted or rotated relative to the bone fastener 102 into the desired alignment for the fixation procedure. Once the aligned, the connecting rod 20 can be coupled to a desired number of multiplanar bone anchor systems 200.

Figure 15:
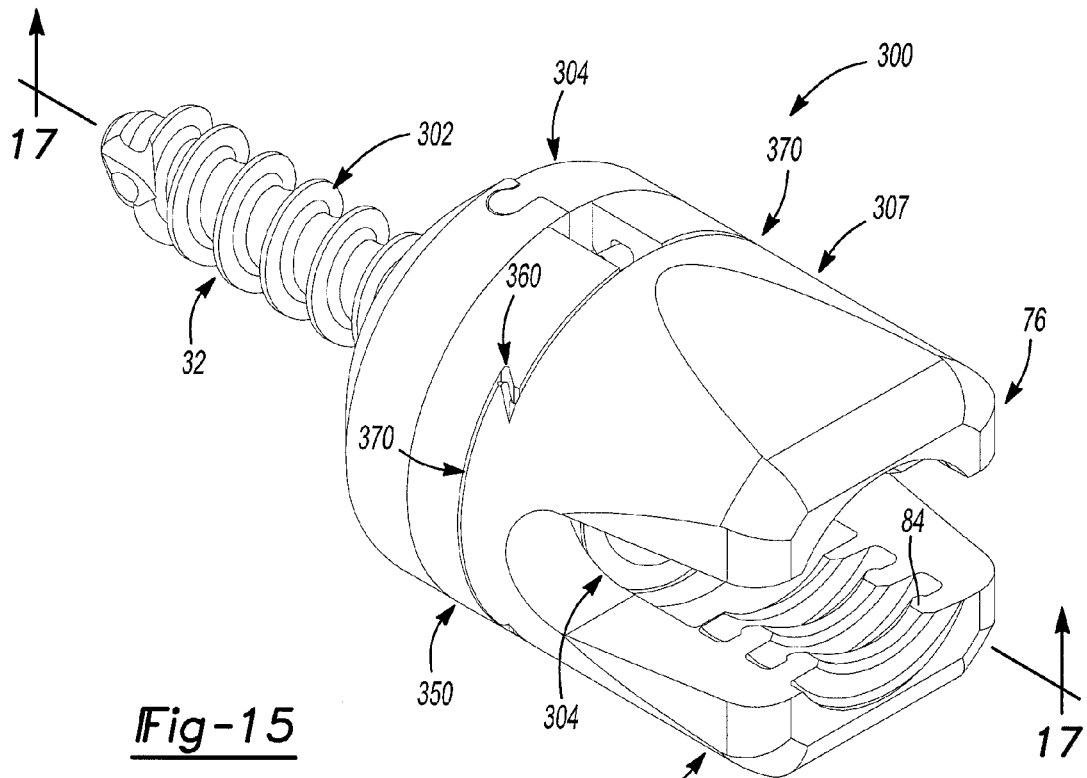
FIG. 15 is a schematic perspective illustration of another exemplary multiplanar bone anchor system for use with a connecting device in a fixation procedure according to the present teachings.
Figure 17:
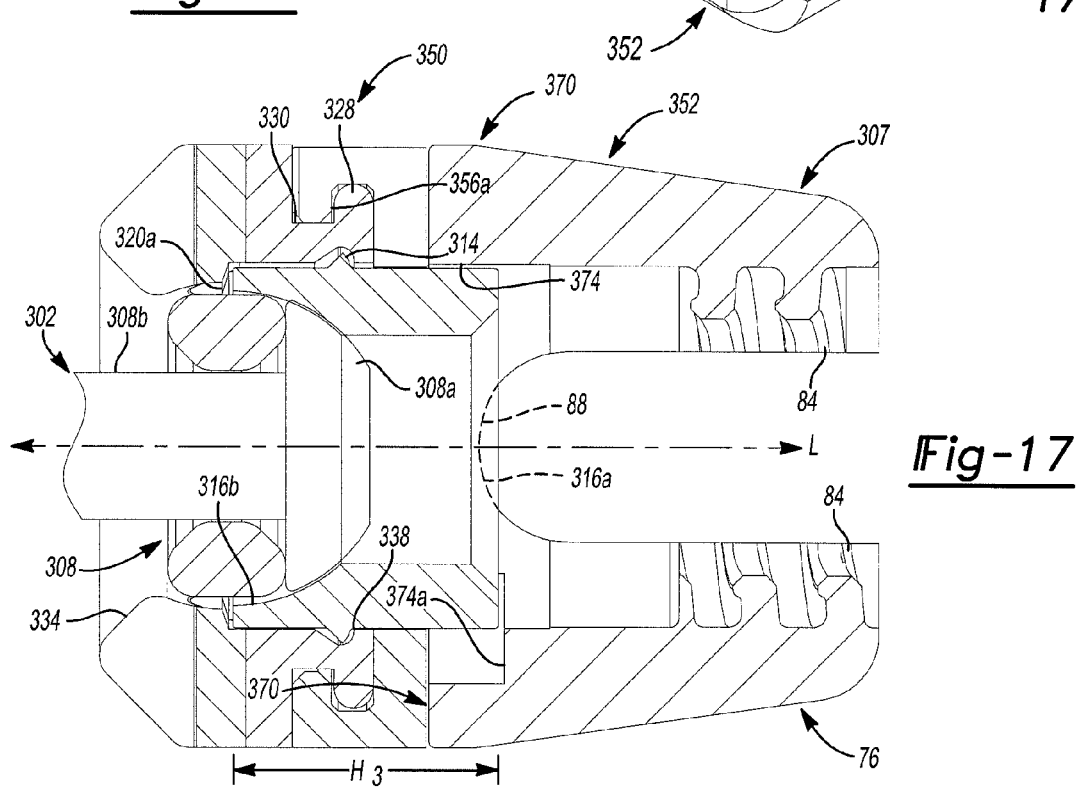
FIG. 17 is a schematic, cross-sectional illustration of the multiplanar bone anchor system of FIG. 15, taken along line 17-17 of FIG. 15.
Figure 16:
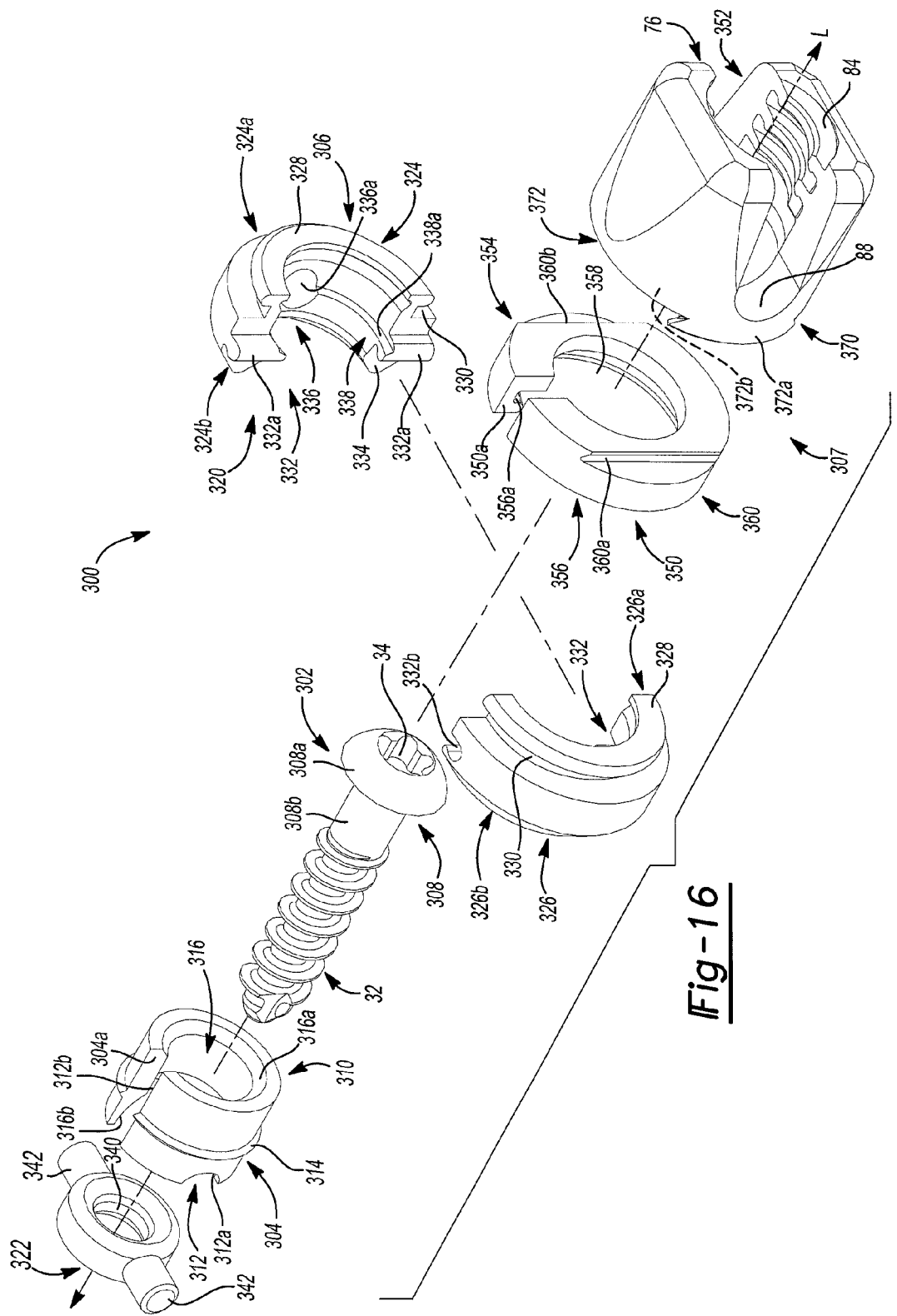
FIG. 16 is an exploded view of the multiplanar bone anchor system of FIG. 15.

With reference now to FIGS. 15-17, in one example, a multiplanar bone anchor system 300 can be employed with the connecting rod 20 to repair a damaged portion of an anatomy. As the multiplanar bone anchor system 300 can be similar to the multiplanar bone anchor system 10 described with reference to FIGS. 1-9, only the differences between the multiplanar bone anchor system 300 and the multiplanar bone anchor system 10 will be discussed in great detail herein, and the same reference numerals will be used to denote the same or similar components. The multiplanar bone anchor system 300 can include a bone fastener 302, a lock ring 304, a multiplanar coupling arrangement or system 306 and a saddle 307.

With reference to FIGS. 15 and 16, the bone fastener 302 can be configured to engage the anatomy to couple the multiplanar bone anchor system 300 to the anatomy. The bone fastener 302 can be composed of any suitable biocompatible material, such as titanium, stainless steel, biocompatible polymers, etc. The bone fastener 302 can include a proximal end or head 308 and the distal end or shank 32. The head 308 can include a generally arcuate or hemispherical portion 308a coupled to the shank 32 via a shaft 308b. The hemispherical portion 308a can include the driver connection feature 34. The hemispherical portion 308a can be coupled to the lock ring 304 when the multiplanar bone anchor system 300 is assembled. The shaft 308b can be generally cylindrical, and can extend distally from the hemispherical portion 308a. The shaft 308b can receive a portion of the multiplanar coupling system 306 to couple the multiplanar coupling system 306 to the bone fastener 302.

The lock ring 304 can be positioned about the head 308 of the bone fastener 302, as best shown in FIG. 17. The lock ring 304 can couple or lock the bone fastener 302 relative to the multiplanar coupling system 306 via a force applied by the connecting rod 20, as will be discussed herein. The lock ring 304 can be generally cylindrical, and can have a height H3. The height H3 can be sized to extend above or about equal to a receiver surface 88 of the saddle 307 so that coupling the connecting rod 20 to the saddle 307 can compress the lock ring 304 onto the head 308 of the bone fastener 302. In this example, as shown in FIG. 16, the lock ring 304 can include a cut out 304a, which can facilitate positioning the lock ring 304 about the head 308 of the bone fastener 302. It should be understood, however, that the cut out 304a can be optional, as the lock ring 304 can have a continuous, uninterrupted cylindrical body. In addition, the lock ring 304 can include a proximal end 310, a distal end 312, a flange 314 and a bore 316.

The proximal end 310 can extend above the receiver surface 88 of the saddle 307 when the multiplanar bone anchor system 300 is assembled. The proximal end 310 can contact at least a portion of the connecting rod 20 when the connecting rod 20 is coupled to the multiplanar bone anchor system 300. The distal end 312 can be coupled to the hemispherical portion 308a of the head 308 of the bone fastener 302 when the lock ring 304 is coupled to bone fastener 302. The distal end 312 can include at least one cut-out or recess 312a. In one example, the distal end 312 can include two recesses 312a, 312b. The recesses 312a and 312b can provide clearance for a portion of the multiplanar coupling system 306. Optionally, the recesses 312a and 312b can enable the bone fastener 302 to move or pivot about the head 308a of the bone fastener 302, as discussed with regard to FIGS. 1-9.

The flange 314 can be formed between the proximal end 310 and the distal end 312, and can extend outwardly about an exterior circumference of the lock ring 304. The flange 314 can cooperate with a portion of the multiplanar coupling system 306 to couple or retain the lock ring 304 within the multiplanar coupling system 306.

The bore 316 can be disposed about a central axis of the lock ring 304. The bore 316 can extend from the proximal end 310 to the distal end 312. The bore 316 can include a first countersink 316a formed near or at the proximal end 310 and a second countersink 316b formed near or at the distal end 312. The first countersink 316a can be configured to at least partially receive a portion of the connecting rod 20 when the connecting rod 20 is coupled to the multiplanar bone anchor system 300. The second countersink 316b can comprise a bearing surface, which can be slidably coupled to the head 308 of the bone fastener 302. Generally, the second countersink 316b can enable the head 308 to move, rotate and/or pivot relative to the lock ring 304.

The multiplanar coupling system 306 can include a connecting arm 320 and a ring 322. The connecting arm 320 can cooperate with the bone fastener 302 to enable the bone fastener 302 to move relative to the saddle 307. It should be noted that although the multiplanar coupling system 306 is described and illustrated herein as including the connecting arm 320 and the ring 322, the multiplanar coupling system 306 could include only a ring or only a connecting arm, if desired. In this example, the connecting arm 320 can have a first shell half 324 and a second shell half 326, which can cooperate to form a substantially continuous annular or cylindrical body having a bore 320a when assembled together (FIG. 17). Each of the first shell half 324 and the second shell half 326 can include a flange 328, a channel 330, at least one mating feature 332, a stop 334, a ring coupling portion 336 and a lock ring retaining portion 338. Generally, each of the flange 328 and the channel 330 can be formed on an exterior surface of each of the first shell half 324 and the second shell half 326, while the stop 334, the ring coupling portion 336 and the lock ring retaining portion 338 can be formed on an interior surface of the first shell half 324 and the second shell half 326.

With reference to FIG. 16, the flange 328 can be defined at a proximal end 324a, 326a of the first shell half 324 and the second shell half 326. The flange 328 can have a smaller diameter than the body of the first shell half 324 and the second shell half 326. The flange 328 can cooperate with the channel 330 to couple a portion of the saddle 307 to the connecting arm 320. The channel 330 can be defined adjacent to the flange 328. The channel 330 can have a diameter that can be smaller than the flange 328. As will be discussed, the flange 328 and the channel 330 can cooperate to rotatably couple a portion of the saddle 307 to the connecting arm 320.

With continued reference to FIG. 16, the at least one mating feature 332 can couple the first shell half 324 and the second shell half 326 together. In one example, the at least one mating feature 332 can comprise two mating features 332, however, it should be understood that any number of mating features could be employed to couple the first shell half 324 to the second shell half 326. For example, a mating portion 332a of the first shell half 324 can comprise a plug, and a mating portion 332b of the second shell half 326 can comprise a receiver. It should be noted that the use of a plug and a receiver is merely exemplary as any suitable technique could be used to couple the first shell half 324 to the second shell half 326, such as adhesives, mechanical fasteners, welding, etc. When the first shell half 324 and the second shell half 326 are coupled together via the mating portions 332, the first shell half 324 and the second shell half 326 can define the bore 320a. The stop 334, the ring coupling portion 336 and the lock ring coupling portion 338 can generally be defined within the bore 320a.

The stop 334 can comprise a tapered portion, which can be formed near or at a distal end 324b, 326b of the first shell half 324 and the second shell half 326. The stop 334 can serve to limit the range of motion of the bone fastener 302 relative to the connecting arm 320. The ring coupling portion 336 can be defined between the proximal end 324a, 326a and the distal end 324b, 326b. In one example, the ring coupling portion 336 can comprise a bore 336a. The bore 336a of the ring coupling portion 336 can receive a portion of the ring 322 to couple the ring 322 to the connecting arm 320, as will be discussed in detail further herein.

The lock ring retaining portion 338 can be defined between the proximal end 324a, 326a and the ring coupling portion 336 of the first shell half 324 and the second shell half 326. The lock ring retaining portion 338 can include a bearing surface 338a. The bearing surface 338a can be defined radially about the interior of the first shell half 324 and the second shell half 326, such that when the first shell half 324 is coupled to the second shell half 326, the bearing surface 338a can extend circumferentially about the bore 320a. The bearing surface 338a can be configured to receive at least a portion of the flange 314 of the lock ring 304 to couple the lock ring 304 to the connecting arm 320.

The ring 322 can be coupled to the connecting arm 320 via the ring coupling portion 336. The ring 322 can be disposed about the head 308 of the bone fastener 302 to enable the bone fastener 302 to move or rotate relative to the saddle 307. The ring 322 can be annular, and can be sized to fit within the connecting arm 320 to enable the connecting arm 320 to move or rotate with the bone fastener 302 relative to the saddle 307. The ring 322 can include a bore 340 and at least one wing 342. The bore 340 can be sized to enable the ring 322 to be coupled about the shaft 308b of the bone fastener 302, but can also be sized so as to prevent the ring 322 from migrating onto the hemispherical portion 308a of the head 308 of the bone fastener 302.

The at least one wing 342 can extend outwardly from a circumference of the ring 322. In this example, the at least one ring 342 can comprise two wings 342. The wings 342 can extend outwardly from generally opposite sides of the ring 322. The wings 342 can be generally cylindrical in shape, and can be sized to be coupled to or received within the bore 336a of the ring coupling portion 336. It should be noted that the shape of the wings 342 described and illustrated herein is merely exemplary, as the wings 342 could have any shape that enables the bone fastener 302 to be coupled to the connecting arm 320, such as elliptical, circular, rounded square, rounded rectangular, etc. The wings 342 can couple the ring 322 to the connecting arm 320 so that the connecting arm 320 can rotate with the bone fastener 302 relative to the saddle 307.

With reference to FIGS. 16 and 17, the saddle 307 can be coupled to the multiplanar coupling system 306 via the connecting arm 320. Generally, the saddle 307 can be coupled to the connecting arm 320 so that the connecting arm 320 can move or rotate relative to the saddle 307, and so that the saddle 307 can move or translate relative to the multiplanar coupling system 306 and the bone fastener 302.

The saddle 307 can be substantially U-shaped and symmetrical with respect to a longitudinal axis L defined by the multiplanar bone anchor system 300 (FIG. 17). The saddle 307 can include a first portion or bottom portion 350, and a second portion or top portion 352. The top portion 352 can move or translate relative to the bottom portion 350.

In this regard, with reference to FIGS. 16 and 17, the bottom portion 350 of the saddle 307 can be generally annular or cylindrical in shape, and can comprise a proximal end 354, a distal end 356 and a bore 358. The bottom portion 350 can also include a cut out 350a, if desired, which can facilitate coupling the bottom portion 350 to the connecting arm 320. It should be noted, that the cut out 350a is optional, as the bottom portion 350 could be coupled to the connecting arm 320 via other techniques, such as a snap-fit, press-fit, etc. The proximal end 354 can be coupled to the top portion 352 of the saddle 307, while the distal end 356 can be coupled to the connecting arm 320. The bore 358 can be sized to allow at least a portion of the proximal end 310 of the lock ring 304 to pass there through. As will be discussed, the bore 358 can also be configured to receive a portion of the connecting arm 320 therein, when the connecting arm 320 is coupled to the bottom portion 350.

In one example, the proximal end 354 of the bottom portion 350 can define at least one rail 360, which can cooperate with the top portion 352 of the saddle 307 to enable the saddle 307 to move or translate relative to the connecting arm 320. In this example, the proximal end 354 can define two rails 360a, 360b, which can be disposed on generally opposite sides of the bore 358. In on example, the rails 360a, 360b can extend along a plane generally perpendicular to the longitudinal axis L of the multiplanar bone anchor system 300, however, it should be understood that the rails 360a, 360b can extend in any desired plane or in multiple planes. The rails 360a, 360b can enable the saddle 307 to move, translate or slide along the proximal end 354 of the bottom portion 350.

The distal end 356 of the bottom portion 350 can define a lip 356a. The lip 356a can extend about the circumference of the bottom portion 350. The lip 356a can project into the bore 358, and can couple the distal end 356 of the bottom portion 350 to the connecting arm 320. In this regard, the lip 356a can be configured to be coupled to the flange 328 of the connecting arm 320. The engagement of the lip 356a with the flange 328 can allow the connecting arm 320 to move or rotate with the bone fastener 302, relative to at least the top portion 352 of the saddle 307, as will be discussed further herein.

The top portion 352 of the saddle 307 can be coupled to the rails 360a, 360b of the proximal end 360 of the bottom portion 350 so that the top portion 352 can move relative to the bottom portion 350. The top portion 352 can be substantially U-shaped and symmetrical with respect to a longitudinal axis L defined by the multiplanar bone anchor system 300. The top portion 352 can include the first or proximal end 76 and a second or distal end 370.

With reference to FIG. 17, the distal end 370 of the top portion 352 can be generally rectangular, and can include the first or receiver surface 88, a second or bottom surface 372 and a central bore 374. The bottom surface 372 can include at least one or more guides 372a. In this example, the bottom surface 90 can include two guides 372a, 372b. The guides 372a, 372b can slidably couple the top portion 352 to the bottom portion 350. In this regard, each guide 372a, 372b can cooperate with a respective one of the rails 360a, 360b to enable the top portion 352 of the saddle 307 to move or translate relative to the bottom portion 350 of the saddle 307. Generally, each guide 372a, 372b can comprise a dovetail shape.

It should be understood, however, that although the top portion 352 and the bottom portion 350 are illustrated and described herein as including rails and guides to enable the relative motion, any suitable device or mechanism could be used to enable the relative motion between the top portion 352 and the bottom portion 350, such as a monorail assembly, bearing, cam surface, etc. It should also be understood that the rails 360a, 360b of the bottom portion 350 could be interchanged with the guides 372a, 372b of the top portion 352, if desired.

With reference to FIGS. 15-17, in order to assemble the multiplanar bone anchor system 300, the ring 322 can be coupled to the shaft 308b of the bone fastener 302. Then, the lock ring 304 can be positioned on the head 308 of the bone fastener 302. Next, the first shell half 324 and the second shell half 326 of the connecting arm 320 can be coupled to the ring 322 and the lock ring 304. The bottom portion 350 of the saddle 307 can then be coupled to the connecting arm 320, such that the connecting arm 320 can move or rotate relative to the bottom portion 350 of the saddle 307. Next, the top portion 352 of the saddle 307 can be coupled to the bottom portion 350 so that the guides 372a, 372b are movably or slidably coupled to the guides 372a, 372b of the connecting arm 320. Note that the movement of the top portion 352 relative to the bottom portion 350 can be limited by contact between the recess 374a of the bore 374 and the lock ring 304.

Once assembled, the connecting arm 320 can cooperate with the bone fastener 302 to enable movement or rotation of the bone fastener 302 about the central or longitudinal axis of the bone fastener 302, which provides a first plane of motion. The bottom portion 350 of the saddle 307 can also rotate relative to the bone fastener 302, and thus, the top portion 352 of the saddle 307 can rotate relative to the bone fastener 302 to thereby define a second plane of motion. In addition, the top portion 352 can also move or translate relative to the bottom portion 350, which can thereby define a third plane of motion. Therefore, when assembled, the multiplanar bone anchor system 300 can have at least three degrees or planes of motion. By allowing the multiplanar bone anchor system 300 to move in at least three planes, the surgeon can manipulate the multiplanar bone anchor system 300 as necessary to conform to the anatomy of the patient.

As the surgical insertion and use of the multiplanar bone anchor system 300 in a fixation procedure can be similar to the surgical insertion and insertion of the multiplanar bone anchor system 10 in a fixation procedure, the surgical insertion and use of the multiplanar bone anchor system 300 will not be discussed in great detail herein. Briefly, however, once the multiplanar bone anchor system 300 is secured to the anatomy, the multiplanar coupling system 306 and the saddle 307 can be moved, rotated or translated relative to the bone fastener 302 into the desired alignment for the fixation procedure. Once the aligned, the connecting rod 20 can be coupled to a desired number of multiplanar bone anchor systems 300.

Figure 18:
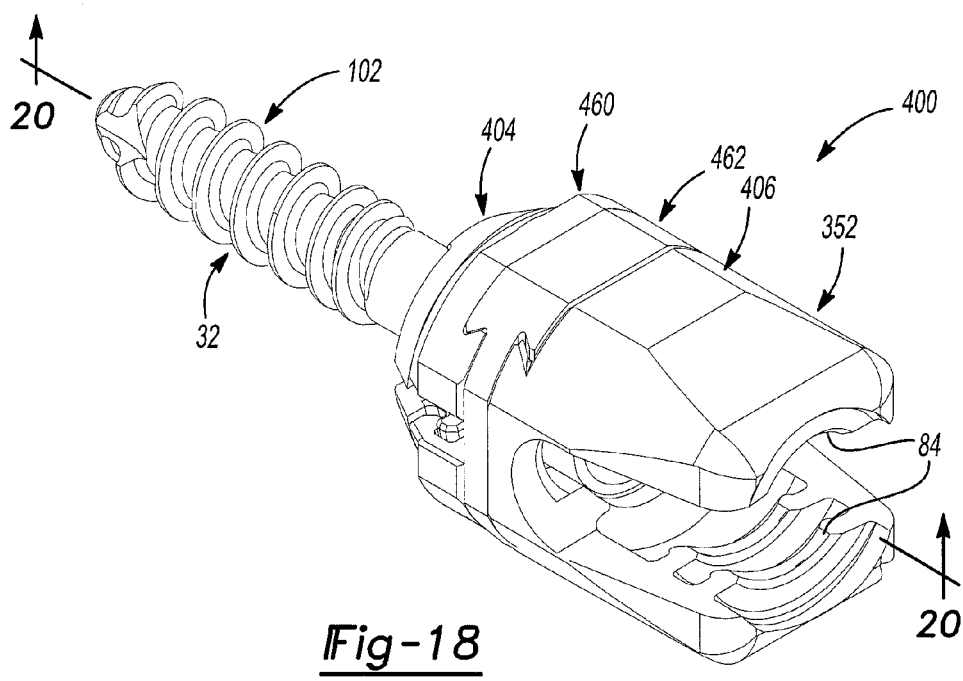
FIG. 18 is a schematic perspective illustration of another exemplary multiplanar bone anchor system for use with a connecting device in a fixation procedure according to the present teachings.
Figure 20:
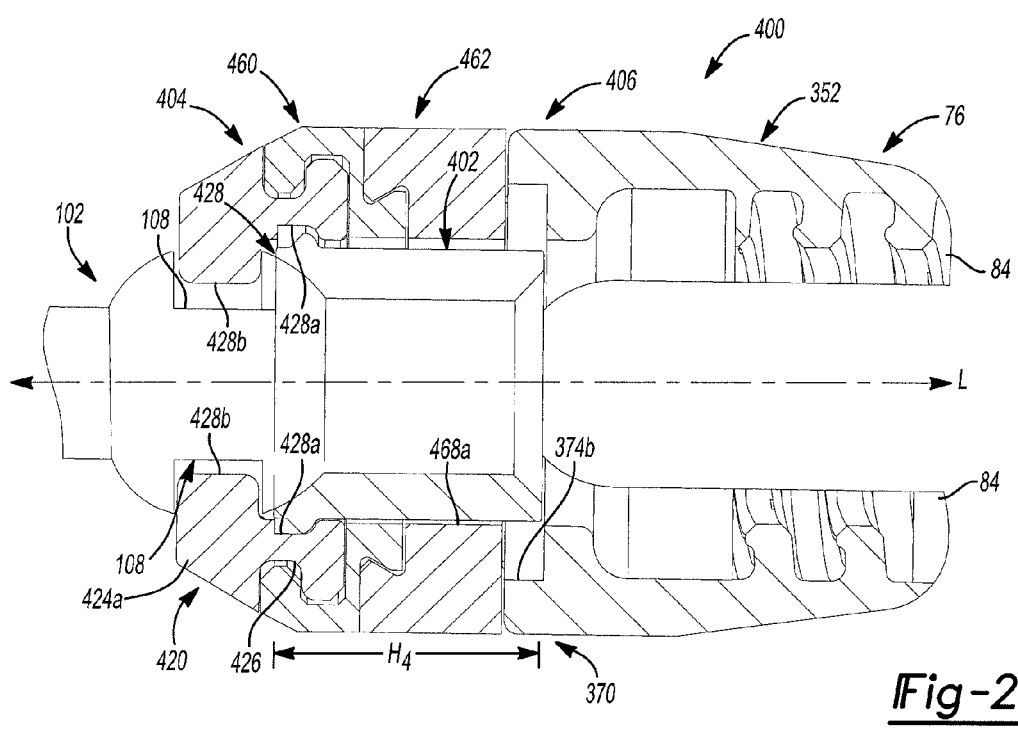
FIG. 20 is a schematic, cross-sectional illustration of the multiplanar bone anchor system of FIG. 18, taken along line 20-20 of FIG. 18.
Figure 19:
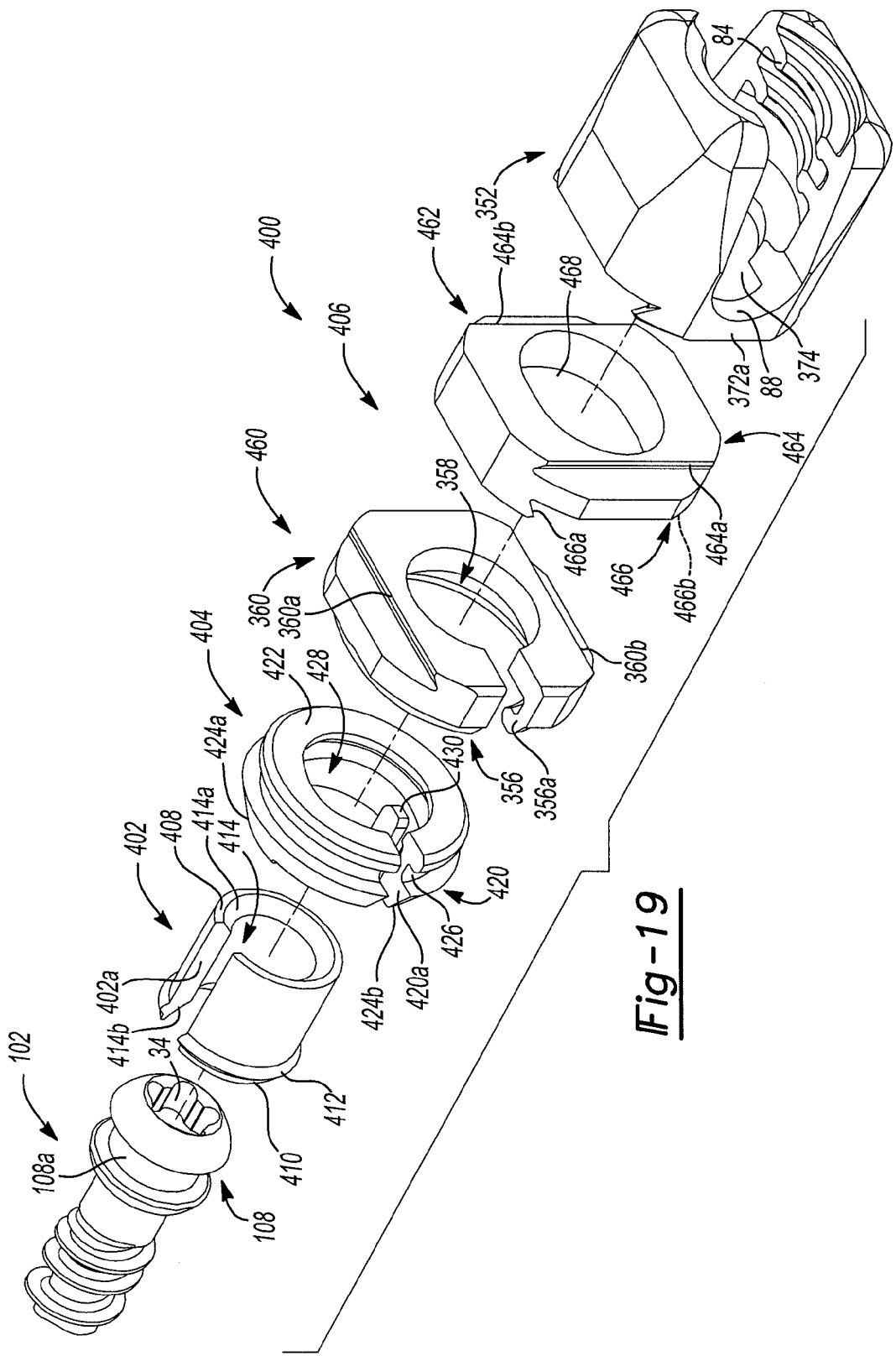
FIG. 19 is an exploded view of the multiplanar bone anchor system of FIG. 18.

With reference now to FIGS. 18-20, in one example, a multiplanar bone anchor system 400 can be employed with the connecting rod 20 to repair a damaged portion of an anatomy. As the multiplanar bone anchor system 400 can be similar to the multiplanar bone anchor system 100, 300 described with reference to FIGS. 9-11 and 15-17, only the differences between the multiplanar bone anchor system 100, 300 and the multiplanar bone anchor system 400 will be discussed in great detail herein, and the same reference numerals will be used to denote the same or similar components. The multiplanar bone anchor system 400 can include the bone fastener 102, a lock ring 402, a multiplanar coupling arrangement or system 404 and a saddle 406.

The lock ring 402 can be positioned about the head 108 of the bone fastener 102. The lock ring 402 can couple or lock the bone fastener 102 relative to the multiplanar coupling system 404 via a force applied by the connecting rod 20, as will be discussed herein. As best shown in FIG. 20, the lock ring 402 can be generally cylindrical, and can have a height H4. The height H4 be sized to extend above or about equal to the receiver surface 88 of the saddle 406 so that coupling the connecting rod 20 to the saddle 406 can compress the lock ring 402 onto the head 108 of the bone fastener 102. In this example, with reference to FIG. 19, the lock ring 402 can include a cut out 402a, which can facilitate positioning the lock ring 402 about the head 108 of the bone fastener 102. It should be understood, however, that the cut out 402a can be optional, as the lock ring 402 can have a continuous, uninterrupted cylindrical body. In addition, the lock ring 402 can include a proximal end 408, a distal end 410, a flange 412 and a bore 414.

The proximal end 408 can extend above or at the receiver surface 88 of the saddle 406 when the multiplanar bone anchor system 400 is assembled. The proximal end 408 can contact at least a portion of the connecting rod 20 when the connecting rod 20 is coupled to the multiplanar bone anchor system 400. The distal end 410 can be coupled to the head 108 of the bone fastener 102 when the lock ring 402 is coupled to bone fastener 102. The flange 412 can be formed near or at the distal end 410, and can extend outwardly about an exterior circumference of the lock ring 402. The flange 412 can cooperate with a portion of the multiplanar coupling system 404 to couple or retain the lock ring 402 within the multiplanar coupling system 404.

The bore 414 can be disposed about a central axis of the lock ring 402. The bore 414 can extend from the proximal end 408 to the distal end 410. The bore 414 can include a first countersink 414a formed near or at the proximal end 408 and a second countersink 414b formed near or at the distal end 410. The first countersink 414a can be configured to at least partially receive a portion of the connecting rod 20 when the connecting rod 20 is coupled to the multiplanar bone anchor system 400. The second countersink 414b can comprise a bearing surface, which can be slidably coupled to the head 108 of the bone fastener 102. Generally, the second countersink 414b can enable the head 108 to move, rotate and/or pivot relative to the lock ring 402.

The multiplanar coupling system 404 can include a connecting arm 420. The connecting arm 420 can cooperate with the bone fastener 102 to enable the bone fastener 102 to move relative to the saddle 406. It should be noted that although the multiplanar coupling system 404 is described and illustrated herein as including only a connecting arm 420, the multiplanar coupling system 404 could include a ring, if desired. In this example, the connecting arm 420 can have a cylindrical body, which can include a cut out 420a. The cut out 420a can facilitate the coupling of the connecting arm 420 to the head 108 of the bone fastener 302. For example, the cut out 420a can enable the connecting arm 420 to be snap-fit around the head 108 of the bone fastener 102. It should be noted, however, that the cut out 410a can be optional, as the connecting arm 410 could have a continuous, uninterrupted cylindrical body. In the case of a continuous, uninterrupted cylindrical body, the connecting arm 420 could be threaded over the shank 32 of the bone fastener 102 into engagement with the head 108 of the bone fastener 102.

In this example, the connecting arm 420 can further comprise a first or proximal end 422, a second or distal end 424, a channel 426, a bore 428 and a coupling feature 430. The proximal end 422 can have a generally smooth surface, which can be positioned adjacent to a portion of the saddle 406 when the multiplanar bone anchor system 400 is assembled. The distal end 424 can be positioned opposite the proximal end 422, and generally, the distal end 424 can comprise a taper 424a. The taper 424a can provide the connecting arm 420 with atraumatic edges.

The channel 426 can be defined between the proximal end 422 and the distal end 424. The channel 426 can extend about an exterior circumference of the cylindrical body of the connecting arm 420. The channel 426 can receive a portion of the saddle 406 to couple the connecting arm 420 to the saddle 406, as will be discussed in detail further herein.

The bore 428 can be defined about a central axis of the connecting arm 420. The bore 428 can receive at least a portion of the lock ring 402 and at least a portion of the bone fastener 102 therein to couple each of the lock ring 402 and the bone fastener 102 to the connecting arm 420. In this regard, with reference to FIG. 20, the bore 428 can include a lock ring coupling portion 428a and a bone fastener coupling portion 428b. In one example, the lock ring coupling portion 428a can comprise a recess, which can be configured to engage the flange 412 of the lock ring 402. The engagement of the flange 412 of the lock ring 402 with the lock ring coupling portion 428a can couple or retain the lock ring 402 within the connecting arm 420. The bone fastener coupling portion 428b can comprise an annular or circumferential projection, which can extend about a circumference of the bore 428. Generally, the bone fastener coupling portion 428b can be sized so as to engage the channel 108a formed in the head 108 of the bone fastener 102 so that the bone fastener 102 can move or rotate relative to the connecting arm 420. Thus, the bone fastener coupling portion 428b can comprise a bearing surface, which can enable the bone fastener 102 to move or rotate relative to the connecting arm 420.

The coupling feature 430 can be formed adjacent to the slot 420a, and generally, can be formed to engage the channel 108a of the bone fastener 102. The engagement of the coupling feature 430 with the channel 108a can enable the multiplanar coupling system 404 to move (rotate and pivot) relative to the bone fastener 102. It should be noted, however, that the coupling feature 430 can be optional, as any suitable device or technique could be used to allow the multiplanar coupling system 404 to move (rotate and pivot) relative to the bone fastener 102, such as a ring with wings, as discussed previously herein.

The saddle 406 can be coupled to the multiplanar coupling system 404 via the connecting arm 420. Generally, the saddle 406 can be coupled to the connecting arm 420 so that the connecting arm 420 can move or rotate relative to the saddle 406, and so that the saddle 406 can move or translate relative to the multiplanar coupling system 404 and the bone fastener 102.

The saddle 406 can be substantially U-shaped and symmetrical with respect to a longitudinal axis L defined by the multiplanar bone anchor system 400 (FIG. 20). The saddle 406 can include a first portion or bottom portion 460, the second portion or top portion 352 and a third portion or middle portion 462. The top portion 352 can move or translate relative to the middle portion 462.

With reference to FIG. 19, the bottom portion 460 of the saddle 406 can be substantially similar to the bottom portion 350 of the saddle 307 described with reference to FIGS. 15-17, and thus, only the differences between the bottom portion 460 of the saddle 406 and the bottom portion 350 of the saddle 307 will be discussed in great detail herein. In this regard, the bottom portion 460 of the saddle 406 can have a substantially different geometric shape than the bottom portion 350 of the saddle 307. For example, the bottom portion 460 can be generally octagonal, such that the rails 360a, 360b associated with the first or proximal end 360 of the bottom portion 460 can be generally rectangular. By having a generally rectangular shape, the rails 360a, 360b of the bottom portion 460 can have a substantially larger length than the rails 360a, 360b of the bottom portion 350. This can enable the saddle 406 to move or translate for a greater distance than the saddle 307. It should be understood, however, that the bottom portion 460 can have the same shape as the bottom portion 350, if desired. The bottom portion 460 of the saddle 406 can be coupled to the connecting arm 420 so that the connecting arm 420 can move or rotate relative to the saddle 406.

In this regard, the channel 426 of the connecting arm 420 can be coupled to the annular lip 356a of the bottom portion 460 such that the annular lip 356a rests in the channel 426 to retain the connecting arm 420 to the bottom portion 460 of the saddle 406. The engagement between the channel 426 and the annular lip 346a can allow the connecting arm 420 to move or rotate with the bone fastener 102, relative to at least the top portion 352 of the saddle 406, as will be discussed further herein.

With reference to FIG. 20, the bottom portion 460 can also include a bore 358, which can be sized to enable at least a portion of the lock ring 402 to pass through the bore 348. In addition, as discussed, the bore 348 can be configured to receive a portion of the connecting arm 420 therein, when the connecting arm 420 is coupled to the bottom portion 460.

With continued reference to FIG. 20, the top portion 352 of the saddle 307 can be coupled to the middle portion 462 so that the top portion 352 can move relative to at least one of the bottom portion 460 and the middle portion 462, as will be discussed in greater detail herein. The middle portion 462 can be coupled between the top portion 352 and the bottom portion 460. Generally, the middle portion 462 can be movable or translatable relative to each of the top portion 352 and the bottom portion 460. The middle portion 462 can be generally octagonal in shape. It should be noted that the shape of the middle portion 462 is merely exemplary, as any suitable shape could be used, such as cylindrical, rectangular, etc. The middle portion 462 can include a first or rail surface 464 opposite a second or guide surface 466 and a bore 468. The bore 468 can be defined about a central axis of the middle portion 462, and can coaxially aligned with the bore 358 of the bottom portion 460 and the bore 374 of the top portion 352. The bore 468 can be sized to enable a portion of the lock ring 402 to extend through the middle portion 462.

The rail surface 464 can include at least one rail 464a. Generally, the rail surface 464 can include two rails 464a, 464b, which can be configured to movably or slidably engage the guides 372a, 372b of the top portion 352. The engagement between the rails 464a, 464b and the guides 372a, 372b can enable the top portion 352 of the saddle 406 to move or translate relative to the middle portion 462 of the saddle 406.

The guide surface 466 can include at least one guide 466a. Generally, the guide surface 466 can include two guides 466a, 466b, which can be configured to movably or slidably engage the rails 360a, 360b of the bottom portion 460 of the saddle 406. The engagement between the guides 466a, 466b and the rails 360a, 360b can enable the bottom portion 460 of the saddle 406 to move or translate relative to the middle portion 462 of the saddle 406.

It should be understood, however, that although the top portion 352, the middle portion 462 and the bottom portion 460 are illustrated and described herein as including rails and guides to enable the relative motion, any suitable device or mechanism could be used to enable the relative motion between the top portion 352, the middle portion 462 and the bottom portion 460, such as a monorail assembly, etc. It should also be understood that the guides 372a, 372b, 466a, 466b of the top portion 352 and the middle portion 462 could be interchanged with the rails 360a, 360b, 464a, 464b of the bottom portion 350 and the middle portion 462, if desired.

With reference to FIGS. 19 and 20, in order to assemble the multiplanar bone anchor system 400, the connecting arm 420 can be coupled to the channel 108a of the bone fastener 102. Then, the lock ring 402 can be coupled to the connecting arm 420. Next, the bottom portion 460 of the saddle 406 can be coupled to the connecting arm 420, such that the connecting arm 420 can move or rotate relative to the bottom portion 460 of the saddle 406. The middle portion 462 can be coupled to the rails 360a, 360b of the bottom portion 460 of the saddle 406 to enable the middle portion 462 to move or translate relative to the bottom portion 460. Note that the movement of the middle portion 462 relative to the bottom portion 460 can be limited by contact between a sidewall 468a of the bore 468 of the middle portion 462 and the lock ring 402 (FIG. 20). Then, the top portion 352 of the saddle 406 can be coupled to the middle portion 462 so that the guides 372a, 372b are slidably coupled to the rails 464a, 464b of the connecting arm 420. Note that the movement of the top portion 352 relative to the middle portion 462 can be limited by contact between a sidewall 374a of the bore 374 of the top portion 352 and the lock ring 402 (FIG. 20).

Once assembled, the connecting arm 420 can cooperate with the bone fastener 102 to enable movement or rotation of the bone fastener 102 about the central or longitudinal axis of the bone fastener 102, which provides a first plane of motion. The bottom portion 460 of the saddle 406 can also rotate relative to the bone fastener 102, and thus, the top portion 352 of the saddle 406 can rotate relative to the bone fastener 102 to thereby define a second plane of motion. In addition, the middle portion 462 can move or translate relative to the connecting arm 420, thereby defining a third plane of motion. As the top portion 352 can also move or translate relative to the middle portion 462, the multiplanar bone anchor system 400 can define a fourth plane of motion. Therefore, when assembled, the multiplanar bone anchor system 400 can have at least four degrees or planes of motion. By allowing the multiplanar bone anchor system 400 to move in at least four planes, the surgeon can manipulate the multiplanar bone anchor system 400 as necessary to conform to the anatomy of the patient.

As the surgical insertion and use of the multiplanar bone anchor system 400 in a fixation procedure can be similar to the surgical insertion and insertion of the multiplanar bone anchor system 300 in a fixation procedure, the surgical insertion and use of the multiplanar bone anchor system 400 will not be discussed in great detail herein. Briefly, however, once the multiplanar bone anchor system 400 is secured to the anatomy, the multiplanar coupling system 404 and the saddle 406 can be moved, rotated or translated relative to the bone fastener 102 into the desired alignment for the fixation procedure. Once the aligned, the connecting rod 20 can be coupled to a desired number of multiplanar bone anchor systems 400.

Figure 21:
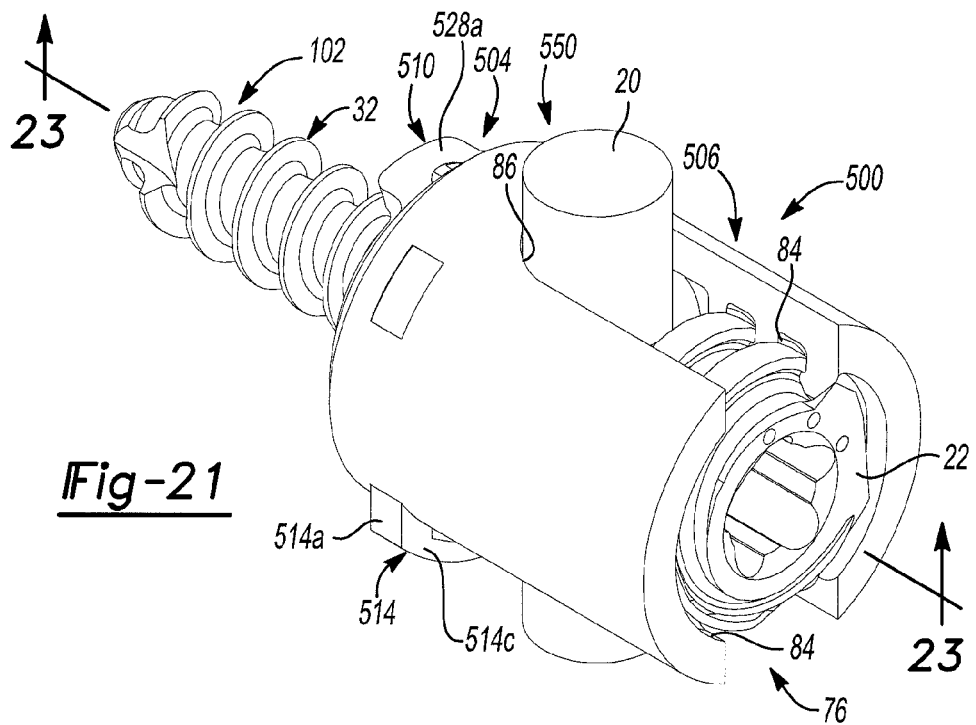
FIG. 21 is a schematic perspective illustration of another exemplary multiplanar bone anchor system for use with a connecting device in a fixation procedure according to the present teachings.
Figure 23:
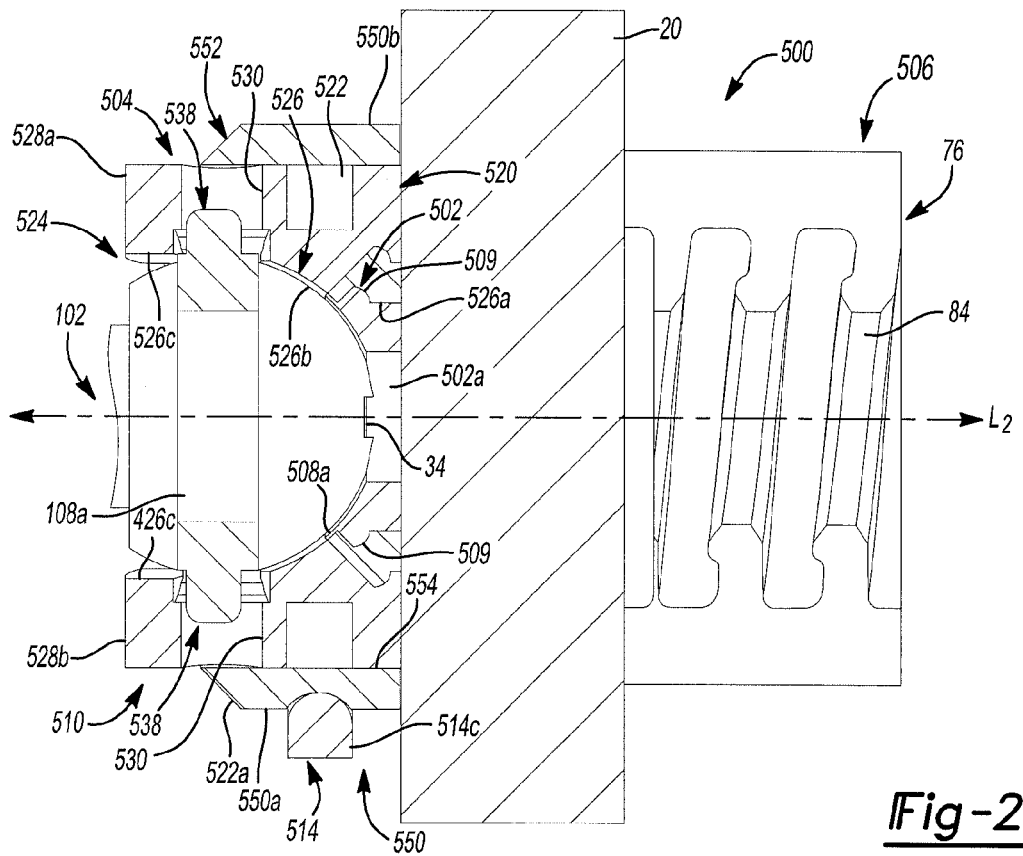
FIG. 23 is a schematic, cross-sectional illustration of the multiplanar bone anchor system of FIG. 21, taken along line 23-23 of FIG. 21.

With reference now to FIGS. 21-23, in one example, a multiplanar bone anchor system 500 can be employed with the connecting rod 20 to repair a damaged portion of an anatomy. As the multiplanar bone anchor system 500 can be similar to the multiplanar bone anchor system 100, 200 described with reference to FIGS. 9-15, only the differences between the multiplanar bone anchor system 100, 200 and the multiplanar bone anchor system 500 will be discussed in great detail herein, and the same reference numerals will be used to denote the same or similar components. The multiplanar bone anchor system 500 can include the bone fastener 102, a lock ring 502, a multiplanar coupling arrangement or system 504 and a saddle 506. It should be noted that although the multiplanar bone anchor system 500 is described and illustrated herein as including the lock ring 502, it should be understood that the multiplanar bone anchor system 500 need not include the lock ring 502. Furthermore, the multiplanar bone anchor system 500 could employ the lock ring 14 instead of the lock ring 502, if desired.

The lock ring 502 can be received within the saddle 506, and can cooperate the multiplanar coupling system 504 and the saddle 506 to fixedly couple or lock the bone fastener 102 into a desired angular position (FIG. 23). In one example, with reference to FIG. 22, the lock ring 502 can include a continuous cylindrical body, which can be formed out of any suitable biocompatible material, such as a biocompatible metal, ceramic, metal alloy, polymer or combinations thereof. The lock ring 502 can include a first or proximal end 507, a second or distal end 508 and a flange 509. In addition, the lock ring 502 can include a bore 502a, which can enable a tool to engage the driver interface feature 34 of the bone fastener 102.

The proximal end 507 of the lock ring 502 can define a first concave surface 507a, which can have a curvature configured to mate with the connecting rod 20. In this regard, the lock ring 502 can support a portion of the connecting rod 20 when the connecting rod 20 is coupled to the multiplanar bone anchor system 500. In this example, the force applied by the set screw 22 to couple the connecting rod 20 to the multiplanar bone anchor system 500 can apply a force to the lock ring 502 to fixedly couple or lock the bone fastener 102 in the desired angular position.

The distal end 508 of the lock ring 502 can apply a force to the head 108 of the bone fastener 102 to fixedly couple or lock the bone fastener 102 in the desired angular position. With reference to FIG. 23, the distal end 508 can define a second concave surface 508a. The concave surface 508a can be configured to mate with the head 108 of the bone fastener 102 to fixedly couple or lock the bone fastener 102 in the desired angular position when the force is applied to the lock ring 502.

The flange 509 can extend about a circumference of the lock ring 502, and can be positioned between the proximal end 507 and the distal end 508 of the lock ring 502. The flange 509 can be integrally formed with the lock ring 502, or could be coupled to the circumference of the lock ring 502 through any suitable manufacturing technique, such as overmolding, adhesives, etc. The flange 509 can be configured to engage a portion of the multiplanar coupling system 504 to couple the lock ring 502 to the multiplanar coupling system 504, as will be discussed in greater detail herein.

With reference to FIGS. 21-23, the multiplanar coupling system 504 can include a connecting arm 510, at least one plug 538 and a retaining clip 514. In one example, the multiplanar coupling system 504 can include two plugs 538. The connecting arm 510 and the plugs 538 can cooperate with the bone fastener 102 to enable the bone fastener 102 to move relative to the saddle 506. The connecting arm 510 can be disposed about a head 30 of the bone fastener 102 to enable the bone fastener 102 to move or articulate relative to the saddle 506. In this example, the connecting arm 510 can be cylindrical, and can be coupled to the saddle 506 via the retaining clip 514, as will be discussed (FIG. 23). The connecting arm 510 can include a first or proximal end 520, a channel 522, a second or distal end 524 and a bore 526.

The proximal end 520 can be received within the saddle 506, when the saddle 506 is coupled to the connecting arm 510 (FIG. 23). The channel 522 can be disposed between the proximal end 520 and the distal end 524. The channel 522 can be received within the saddle 506 and can cooperate with the saddle 506 and the retaining clip 514 to couple the connecting arm 510 to the saddle 506, as will be discussed. A majority of the distal end 524 can be disposed outside of the saddle 506 when the connecting arm 510 is coupled to the saddle 506 (FIG. 23). The distal end 524 can include at least one flange 528.

In one example, with continued reference to FIG. 23, the distal end 524 can include two flanges 528a, 528b. Generally, the flanges 528 can be positioned opposite each other, and can each extend for a length beyond the distal end 524 of the connecting arm 510, as shown in FIG. 22. With reference back to FIG. 23, each of the flanges 528 can include a bore 530. Each of the bores 530 can receive a portion of one of the plugs 538 to couple the bone fastener 102 to the connecting arm 510, as will be discussed in greater detail herein. In one example, the bores 530 can be defined through the circumference of the flanges 528 such that the bores 530 are in communication with the bore 526.

The bore 526 can be defined from the proximal end 520 to the distal end 524. The bore 526 can be formed about a central axis of the connecting arm 510. The bore 526 can receive at least a portion of the lock ring 502 when the multiplanar bone anchor system 500 is assembled. In this regard, with reference to FIG. 23, the bore 526 can include a lock ring coupling portion 526a, a bearing portion 526b and a limiting portion 526c.

The lock ring coupling portion 526a can be formed near or at the proximal end 520. The lock ring coupling portion 526a can be configured to engage the flange 509 of the lock ring 502 to couple the lock ring 502 to the connecting arm 510. In one example, the lock ring coupling portion 526a can comprise a portion of the bore 526 that has a contour that mates with an exterior contour of the lock ring 502, however, it should be understood that the lock ring coupling portion 526a can have any desired configuration operable to retain the lock ring 502 within the connecting arm 510. In this example, the lock ring coupling portion 526a can be formed such that the proximal end 507 of the lock ring 502 extends beyond the proximal end 520 of the connecting arm 510 so that the connecting rod 20 can be received within the concave surface 507a of the lock ring 502.

The bearing portion 526b can be formed adjacent to the proximal end 520 of the connecting arm 510. The bearing portion 526b can be generally concave, and can be configured to mate with at least a portion of the hemispherical head 30 of the bone fastener 102. The bearing portion 526b can enable the bone fastener 102 to move, rotate or articulate relative to the connecting arm 510. The limiting portion 526c can be defined adjacent to the distal end 524 of the connecting arm 510. Although not illustrated herein, the limiting portion 526c can include a taper, if desired. Generally, the limiting portion 526c can limit the range of motion or articulation of the bone fastener 102.

With reference to FIG. 22, the plugs 538 can cooperate with the connecting arm 510 to enable the bone fastener 102 to move or rotate about the longitudinal axis L2 of the bone fastener 102. The plugs 538 can couple the bone fastener 102 to the connecting arm 510. Each of the plugs 538 can include a coupling end 540. The coupling end 540 can couple the plug 538 to the connecting arm 510. The coupling end 540 can include a fastening feature 540a, which can be accessible when the plugs 538 are coupled to the connecting arm 510. The fastening feature 540a can comprise any suitable feature, such as a slot, cut-out or other feature engagable by a tool.

Generally, the fastening feature 540a can enable a tool, such as a driver, to couple the plug 538 to the connecting arm 510 and the head 30 of the bone fastener 12. In addition, if desired, the plugs 538 could be integrally formed with the connecting arm 510. It should be noted that the shape of the plugs 538 is merely exemplary, as the plugs 538 could have any desired shape, such as elliptical, spherical, rounded, annular, cylindrical, rounded square, rounded rectangular, etc. In addition, although not illustrated herein, the plugs 538 can include one or more tapered surfaces, which can enable the bone fastener 102 to move or pivot relative to the connecting arm 510, if desired.

With reference to FIGS. 22 and 23, the retaining clip 514 can couple the saddle 506 to the connecting arm 510. The retaining clip 514 can comprise a substantially U-shaped clip, such as Dutchman clip, for example. As a Dutchman clip can be generally known, the retaining clip 514 will not be discussed in great detail herein. Briefly, however, the retaining clip 514 can define a first arm 514a and a second arm 514b, which can be coupled together via a connector 514c. Each of the first arm 514a and the second arm 514b can include a locking tang T. Generally, the first arm 514a and the second arm 514b can be flexible, so that the retaining clip 514 can be biased into engagement with the saddle 506 and the connecting arm 510. As will be discussed, the retaining clip 514 can be received through a portion of the saddle 506 and through the channel 522 of the connecting arm 510 to movably or rotatably couple the saddle 506 to the connecting arm 510.

The saddle 506 can include the first or proximal end 76 and a second or distal end 550. The distal end 550 can be generally cylindrical, and can include the first or a receiver surface 88, a second or bottom surface 552, a central bore 554 and at least one slot 556.

As best shown in FIG. 23, the bottom surface 552 can include a taper 552a. The taper 552a can provide the bottom surface 552 with atraumatic edges. The central bore 554 can be defined from the receiver surface 88 through to the bottom surface 552 of the saddle 506. The central bore 554 can be configured to receive at least a portion of the connecting arm 510 rotatably therein. Thus, the central bore 554 can have a diameter, which can be slightly greater than a diameter of the connecting arm 510, so that the connecting arm 510 can rotate relative to the saddle 506.

The at least one slot 556 can be defined through a portion of the distal end 550 of the saddle 506. In one example, the at least one slot 556 can comprised two slots 556. The two slots 556 can be formed opposite each other, and can generally be formed a distance apart, with the distance between the two slots 556 about equal to a length of the connector 514c of the retaining clip 514.

The slots 556 can be defined from a first side 550a to a second side 550b of the distal end 550 of the saddle 506. The slots 556 can have a length from the first side 550a to the second side 550b, which can be about equal to a length of the first arm 514a and the second arm 514b. Given the length of the slots 556, the connector 514c of the retaining clip 514 can generally be disposed adjacent to an exterior surface of the distal end 550 of the saddle 506 (FIG. 23). It should be noted, however, that the saddle 506 could be configured so that the connector 514c is received within the saddle 506 when the retaining clip 514 is coupled to the saddle 506 and connecting arm 510.

The slots 556 can each include a tab 556a, which can be formed near the second side 550b of the distal end 550. The tab 556a can cooperate with the tang T of the first arm 514a and the second arm 514b to couple the retaining clip 514 to the saddle 506. By coupling the retaining clip 514 to the saddle 506, the connecting arm 510 can also be coupled to the saddle 506.

In this regard, with reference to FIGS. 22 and 23, in order to assemble the multiplanar bone anchor system 500, the lock ring 502 can be positioned within the bore 526 and coupled to the lock ring coupling portion 526a via the flange 509 of the lock ring 502. With the lock ring 502 coupled to the connecting arm 510, the distal end 550 of the saddle 506 can be positioned onto the proximal end 520 of the connecting arm 510. Next, the bone fastener 102 can be coupled to the connecting arm 510 by snap-fitting, press-fitting or threading the plugs 538 into engagement with the bores 530 of the connecting arm 510 so that the bone fastener 102 can move (rotate and pivot) relative to the connecting arm 510.

With the distal end 550 of the saddle 506 positioned about at least the proximal end 520 of the connecting arm 510, the retaining clip 514 can be inserted into the slots 556 so that the tangs T of the first arm 514a and the second arm 514b can engage the tabs 556a of the slots 556. The first arm 514a and the second arm 514b can be inserted such that the first arm 514a and the second arm 514b can be at least partially retained within the channel 522 of the connecting arm 510. Thus, the retaining clip 514 can be employed to couple the connecting arm 510 and bone fastener 102 to the saddle 506.

Once assembled, the plugs 538 can cooperate with the channel 108 of the bone fastener 102 to enable movement or rotation of the bone fastener 102 about the central or longitudinal axis of the bone fastener 102, thereby providing a first plane of motion. In addition, the retaining clip 514 can enable the connecting arm 510 to move or rotate relative to the saddle 506, thereby defining a second plane of motion. Thus, when assembled, the multiplanar bone anchor system 500 can have at least two planes or degrees of motion. By allowing the multiplanar bone anchor system 500 to move in at least two planes, the surgeon can manipulate the multiplanar bone anchor system 500 as necessary to conform to the anatomy of the patient.

As the surgical insertion and use of the multiplanar bone anchor system 500 in a fixation procedure can be similar to the surgical insertion and insertion of the multiplanar bone anchor system 100, 200 in a fixation procedure, the surgical insertion and use of the multiplanar bone anchor system 500 will not be discussed in great detail herein. Briefly, however, once the multiplanar bone anchor system 500 is secured to the anatomy, the bone fastener 102, the multiplanar coupling system 504 and/or the saddle 506 can be moved or rotated relative to one another until the multiplanar bone anchor system 500 is in the desired alignment for the fixation procedure. Once the aligned, the connecting rod 20 can be coupled to a desired number of multiplanar bone anchor systems 500.

Figure 24:
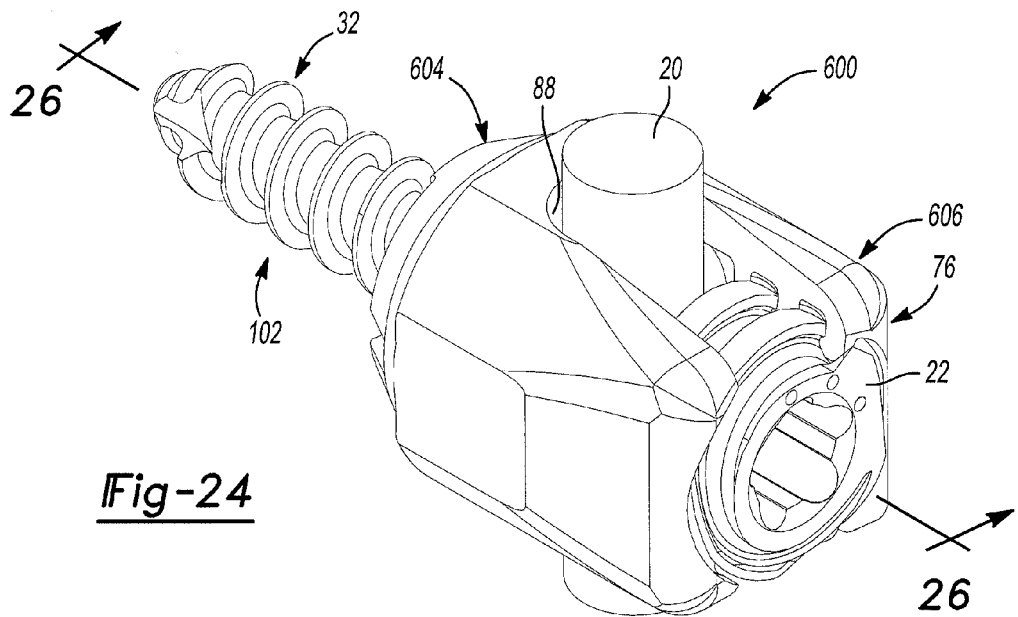
FIG. 24 is a schematic perspective illustration of another exemplary multiplanar bone anchor system for use with a connecting device in a fixation procedure according to the present teachings.
Figure 26:
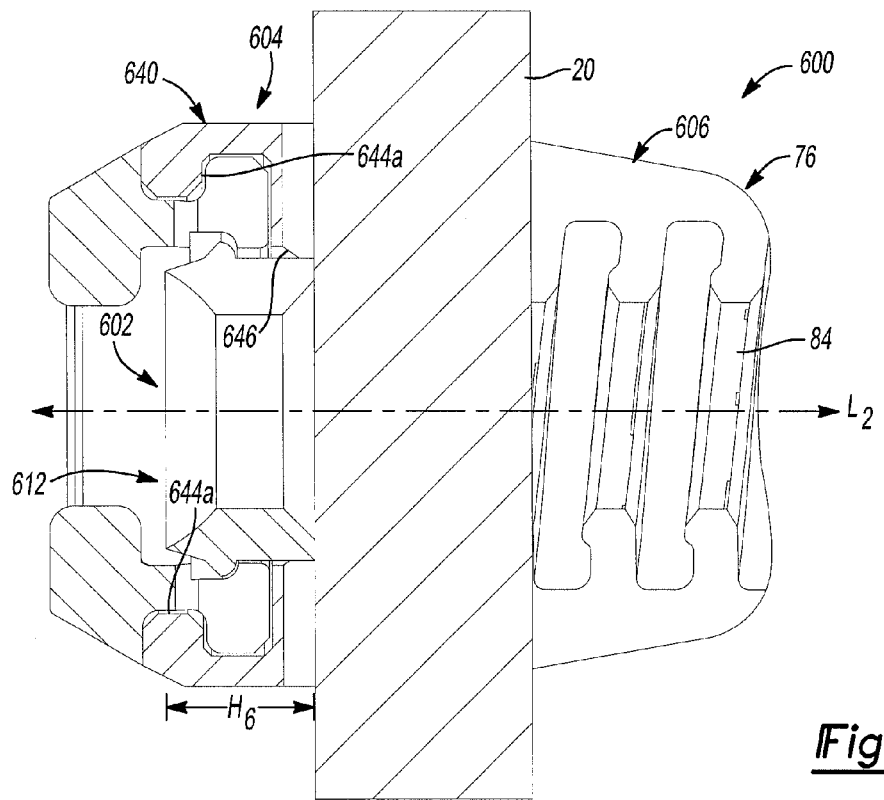
FIG. 26 is a schematic, cross-sectional illustration of the multiplanar bone anchor system of FIG. 24, taken along line 26-26 of FIG. 24.
Figure 25:
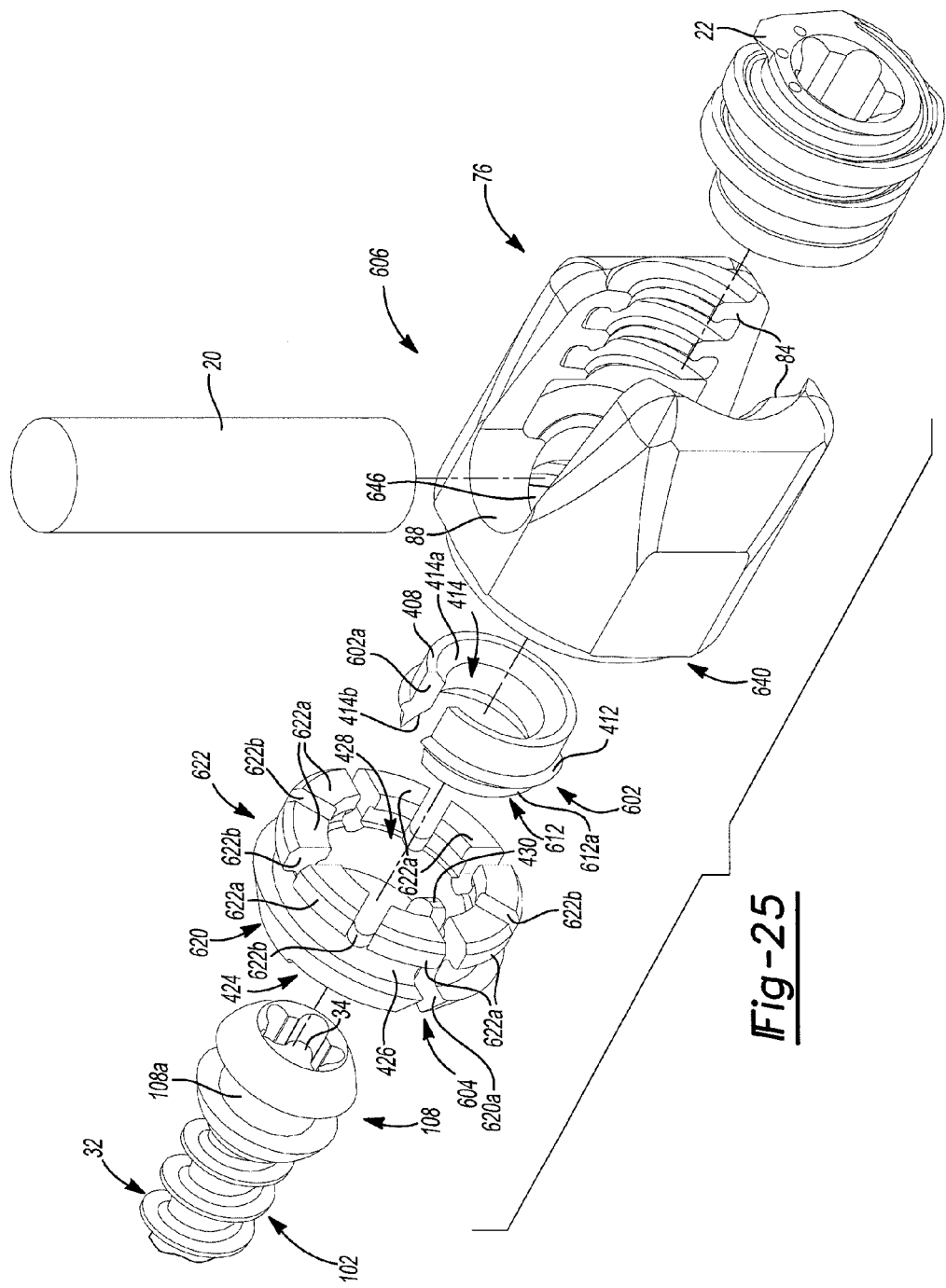
FIG. 25 is an exploded view of the multiplanar bone anchor system of FIG. 24.

With reference now to FIGS. 24-26, in one example, a multiplanar bone anchor system 600 can be employed with the connecting rod 20 to repair a damaged portion of an anatomy. As the multiplanar bone anchor system 600 can be similar to the multiplanar bone anchor system 400 described with reference to FIGS. 18-20, only the differences between the multiplanar bone anchor system 400 and the multiplanar bone anchor system 600 will be discussed in great detail herein, and the same reference numerals will be used to denote the same or similar components. The multiplanar bone anchor system 600 can include the bone fastener 102, a lock ring 602, a multiplanar coupling arrangement or system 604 and a saddle 606.

The lock ring 602 can be positioned about the head 108 of the bone fastener 102. The lock ring 602 can couple or lock the bone fastener 102 relative to the multiplanar coupling system 604 via a force applied by the connecting rod 20, as will be discussed herein. With reference to FIG. 26, the lock ring 602 can be generally cylindrical, and can have a height H6. The height H6 be sized to extend above or about equal to a receiver surface 88 of the saddle 606 so that coupling the connecting rod 20 to the saddle 606 can compress the lock ring 602 onto the head 108 of the bone fastener 102. In this example, the lock ring 602 can include a cut out 602a, which can facilitate positioning the lock ring 602 about the head 108 of the bone fastener 102. It should be understood, however, that the cut out 602a can be optional, as the lock ring 602 can have a continuous, uninterrupted cylindrical body. In addition, the lock ring 602 can include the proximal end 408, a distal end 610, the flange 412 and the bore 414. With reference to FIGS. 25 and 26, the distal end 610 can be coupled to the head 108 of the bone fastener 102 when the lock ring 602 is coupled to bone fastener 102.

The multiplanar coupling system 604 can include a connecting arm 620. The connecting arm 620 can cooperate with the bone fastener 102 to enable the bone fastener 102 to move relative to the saddle 606. It should be noted that although the multiplanar coupling system 604 is described and illustrated herein as including only a connecting arm 620, the multiplanar coupling system 604 could include a ring, such as the ring 322 illustrated in FIG. 16, if desired. In this example, the connecting arm 620 can have a cylindrical body, which can include a cut out 620a. The cut out 620a can facilitate the coupling of the connecting arm 620 to the head 108 of the bone fastener 102. For example, the cut out 620a can enable the connecting arm 620 to be snap-fit around the head 108 of the bone fastener 102. It should be noted, however, that the cut out 620a can be optional, as the connecting arm 620 could have a continuous, uninterrupted cylindrical body. In the case of a continuous, uninterrupted cylindrical body, the connecting arm 620 could be threaded over the shank 32 of the bone fastener 102 into engagement with the head 108 of the bone fastener 102.

In this example, the connecting arm 620 can further comprise a first or proximal end 622, the second or distal end 424, the channel 426, the bore 428 and the tool feature 430. The proximal end 622 can include a plurality of arcuate members 622a, which can each be separated by one or more spaces 622b. The plurality of arcuate members 622a can generally be formed about a circumference of the proximal end 622. The plurality of arcuate members 622a can cooperate with the channel 426 to couple the connecting arm 620 to the saddle 606. The one or more spaces 622b can enable the plurality of arcuate members 620a to be flexible, such that the plurality of arcuate members 620a can be snap-fit into engagement with the saddle 606.

Generally, with reference to FIGS. 25 and 26, the saddle 606 can be coupled to the connecting arm 620 so that the connecting arm 620 can move or rotate relative to the saddle 606. The saddle 606 can be substantially U-shaped and symmetrical with respect to a longitudinal axis L2 defined by the multiplanar bone anchor system 600. The saddle 606 can include the first or proximal end 76 and a second or distal end 640.

With reference to FIG. 25, the distal end 640 of the saddle 606 can be generally rectangular, and can include the first or a receiver surface 88, a second or bottom surface 644 and a bore 646. With reference to FIG. 26, the bottom surface 644 can include a lip 644a. The lip 644a can extend downwardly from the bottom surface 644 about the perimeter of the bottom surface 644. The lip 644a can be configured to be received in the channel 426 so that a portion of the bore 464 can surround the plurality of arcuate members 620a to couple the saddle 606 to the connecting arm 620. This can also enable the saddle 606 to move or rotate relative to the connecting arm 620.

With reference to FIGS. 25 and 26, in order to assemble the multiplanar bone anchor system 600, the connecting arm 620 can be coupled to the channel 108 of the bone fastener 102. Then, the lock ring 602 can be coupled to the connecting arm 620. Next, the distal end 640 of the saddle 606 can be coupled to the connecting arm 620, such that the connecting arm 620 can move or rotate relative to the saddle 606.

Once assembled, the connecting arm 620 can cooperate with the bone fastener 102 to enable movement or rotation of the bone fastener 102 about the central or longitudinal axis of the bone fastener 102, which can provide a first plane of motion. The saddle 606 can also rotate relative to the connecting arm 620, which can thereby define a second plane of motion. In addition, the saddle 606 can rotate relative to the bone fastener 102 to thereby define a third plane of motion. Therefore, when assembled, the multiplanar bone anchor system 600 can have at least three degrees or planes of motion. By allowing the multiplanar bone anchor system 600 to move in at least three planes, the surgeon can manipulate the multiplanar bone anchor system 600 as necessary to conform to the anatomy of the patient.

As the surgical insertion and use of the multiplanar bone anchor system 600 in a fixation procedure can be similar to the surgical insertion and insertion of the multiplanar bone anchor system 400 in a fixation procedure, the surgical insertion and use of the multiplanar bone anchor system 600 will not be discussed in great detail herein. Briefly, however, once the multiplanar bone anchor system 600 is secured to the anatomy, the multiplanar coupling system 604 and the saddle 606 can be moved or rotated relative to the bone fastener 102 into the desired alignment for the fixation procedure. Once the aligned, the connecting rod 20 can be coupled to a desired number of multiplanar bone anchor systems 600.

Accordingly, the multiplanar bone anchor system 10, 100, 200, 300, 400, 500, 600 can be used to repair damaged tissue in the anatomy, such as in the case of a spinal fixation or fusion procedure. By allowing the bone fastener 12, 102, 302 and/or the saddle 18, 106, 206, 308, 406, 506, 606 to move in multiple planes, but in a controlled fashion. In addition, the ability to manipulate the position of the bone fastener 12, 102, 302 and/or the saddle 18, 106, 206, 308, 406, 506, 606 can enable the multiplanar bone anchor system 10, 100, 200, 300, 400, 500, 600 to be used with a variety of different anatomical structures.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

Figure 27:
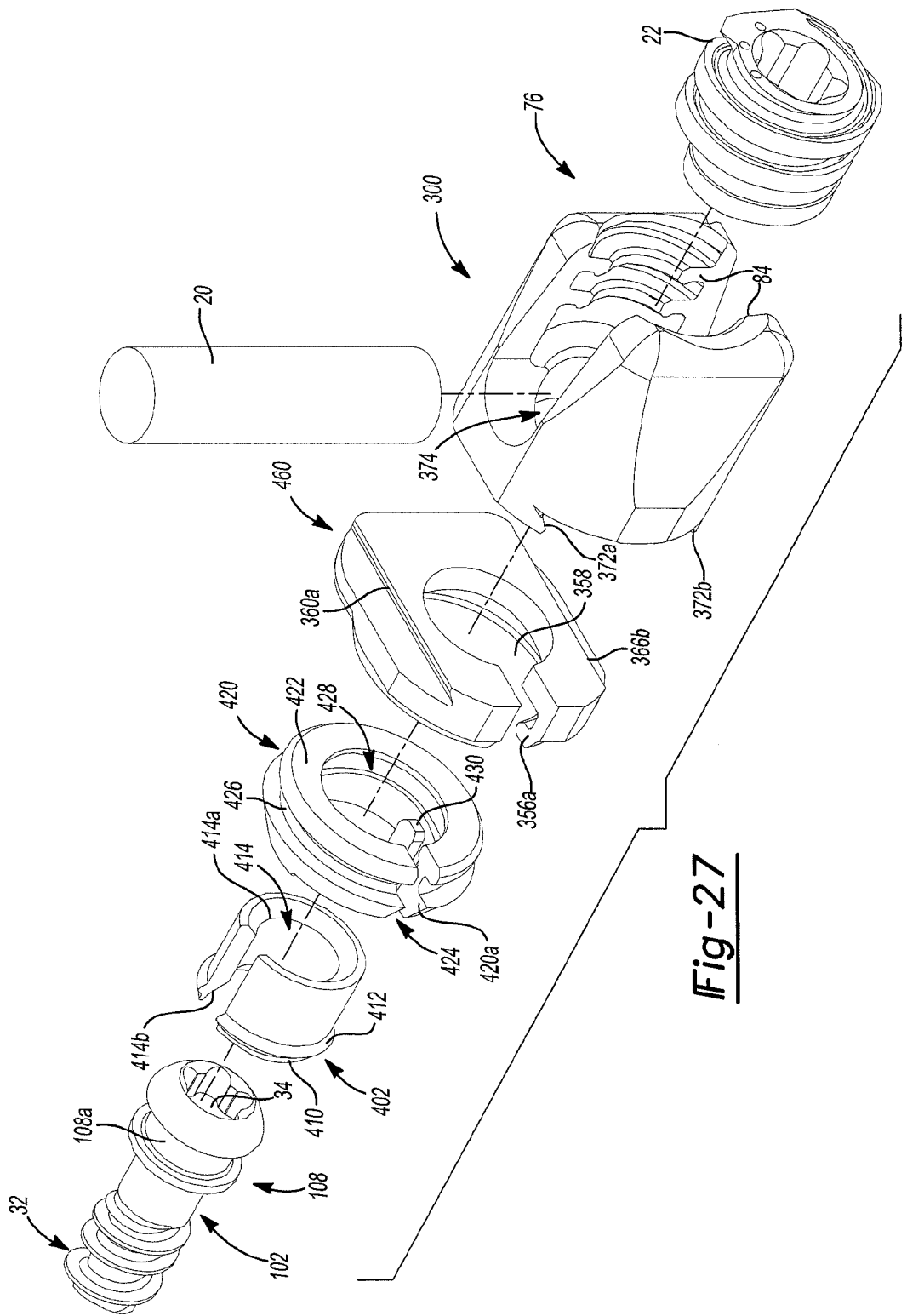
FIG. 27 is a schematic exploded view of another exemplary multiplanar bone anchor system for use with a connecting device in a fixation procedure according to the various teachings.

For example, while the multiplanar bone anchor system 300 has been described herein with reference to FIGS. 15-17 as including the bone fastener 302, the lock ring 304, the connecting arm 320, the ring 322 and the bottom portion 350, those of skill in the art will appreciate that the present disclosure, in its broadest aspects, may be constructed somewhat differently. In this regard, a multiplanar bone anchor system 300' could include the bone fastener 102, the lock ring 402, the connecting arm 420 and the bottom portion 460 associated with the multiplanar bone anchor system 400, as illustrated in FIG. 27. In this example, the multiplanar bone anchor system 300' can provide multiple planes of motion while requiring fewer components, which may be desirable for manufacturing purposes.

As a further example, while the multiplanar bone anchor system 10, 100, 200, 500 has been described herein as having a ring 50, 112, 512, those of skill in the art will appreciate that the present disclosure, in its broadest aspects, may be constructed somewhat differently. In this regard, with reference to FIGS. 28-30, a connecting arm 700 could be employed in place of the ring 50, 112, 512. The connecting arm 700 can cooperate with the bone fastener 102, and can include at least one bore 702 and at least one plug 704. The connecting arm 700 can also include throughbore 706, which can receive the head 108 of the bone fastener 102 therein. The at least one plug 704 can be coupled to the at least one bore 702 of the connecting arm 700 to enable the bone fastener 102 to rotate relative to the connecting arm 700. In this example, the at least one plug 704 can include two plugs 704, which can be received within two opposite bores 702. Each of the plugs 704 can be press fit into the bores 702 so that a bearing surface 704a formed on the plugs 704 can rotate about the channel 108a of the bone fastener 102.

What is claimed is:

1. A multiplanar bone anchor system for a fixation procedure comprising:
    a bone fastener including a head and an end adapted to engage an anatomy;
    a coupling arrangement coupled to the head of the bone fastener so that the bone fastener is rotatable and pivotable relative to the coupling arrangement; and
    a saddle configured to receive a rod along a rod receiving axis, the saddle coupled to the coupling arrangement, the saddle movable relative to at least one of the bone fastener and the coupling arrangement in a direction perpendicular to the rod receiving axis; and
    a connecting arm coupled to the saddle that defines a bearing surface,
    wherein the coupling arrangement further includes a ring coupled about the head of the bone fastener, the ring having at least one wing operable to rotatably couple the ring to the saddle, the at least one wing cooperating with the bearing surface to enable the ring to rotate relative to the saddle.

2. The system of claim 1, wherein the saddle is movable relative to at least one of the bone fastener and the coupling arrangement to define a first plane of motion and wherein the saddle further comprises:
    a first portion coupled to the coupling arrangement; and
    a second portion coupled to the first portion, the second portion movable relative to the first portion to define a second plane of motion.

3. The system of claim 2, wherein the second portion is coupled to the first portion by a retaining clip, a retaining ring, a dovetail connection or combinations thereof.

4. The system of claim 2, wherein one of the first portion of the saddle and the second portion of the saddle includes at least one rail and the other includes at least one guide, and the at least one rail is slidably coupled to the at least one guide to define the first plane of motion.

5. The system of claim 1, further comprising a lock ring coupled to the head of the bone fastener and at least one of the coupling arrangement and the saddle, the lock ring configured to receive a force to lock the position of the bone fastener relative to the saddle.

6. The system of claim 1, wherein the bone fastener comprises a pedicle screw.

7. The system of claim 1, wherein the head of the bone fastener defines a channel, and the coupling arrangement further comprises a connecting arm that defines a coupling portion operable to engage the channel to rotatably couple the connecting arm to the bone fastener.

8. The system of claim 1, wherein the saddle is linearly movable relative to the coupling arrangement.

9. The system of claim 1, wherein the saddle is linearly movable in a predetermined direction relative to the coupling arrangement.

10. The system of claim 1, wherein the coupling arrangement includes at least two components.

11. The system of claim 1, further comprising a rod having a longitudinal axis, the saddle defining a channel receiving the rod, the head of the bone fastener linearly movable relative to the rod in a direction perpendicular to the longitudinal axis of the rod.

12. The system of claim 11, wherein the head of the bone fastener is positionable between the channel and the second end of the bone fastener by linearly translating the coupling arrangement relative to the saddle in the direction perpendicular to the longitudinal axis of the rod.

13. The system of claim 1, wherein the saddle defines a seat for seating the rod, the seat linearly movable relative to the head of the fastener in a direction perpendicular to a longitudinal axis of the rod.

14. The system of claim 1, wherein the bone fastener pivots relative to the coupling arrangement about a pivot axis, the pivot axis being linearly translatable with the coupling arrangement relative to the saddle in the direction perpendicular to the rod receiving axis.

15. The system of claim 1, wherein the saddle includes first and second upwardly extending arms spaced apart in a lateral direction to define an opening for receiving the rod, the saddle movable relative to the head of the bone fastener in the lateral direction.

16. The system of claim 15, wherein the saddle is movable relative to the head of the bone fastener after assembly of the system.

17. A multiplanar bone anchor system for a fixation procedure comprising:
a bone fastener including a head and an end adapted to engage an anatomy;
a coupling arrangement coupled to the head of the bone fastener the coupling arrangement including a ring and a connecting arm, the ring including at least one wing, the ring coupled about at least a portion of the head of the bone fastener, the at least one wing coupling the ring to the connecting arm so that the ring rotates with the connecting arm; and
a saddle including a first portion and a second portion, the first portion configured to receive a rod along a rod receiving axis, the first portion movable relative to the second portion in a direction perpendicular to the rod receiving axis, the bone fastener being pivotable and rotatable relative to the saddle, the first portion including at least one guide and the second portion including at least one rail, the at least one guide of the first portion slidably coupled to the at least one rail of the second portion to enable the first portion to move relative to the second portion.

18. The system of claim 17, wherein the saddle further comprises a third portion that includes at least one guide opposite at least one rail, and the at least one guide of the first portion is slidably coupled to the at least one rail of the third portion so that the first portion is movable relative to the third portion and the at least one rail of the second portion is slidably coupled to the at least one guide of the third portion so that the third portion is movable relative to the second portion.

19. The system of claim 17, wherein the second portion further comprises a bearing surface, and the at least one wing of the ring is coupled to the bearing surface to enable the bone fastener to rotate relative to the second portion.

20. The system of claim 17, wherein the second portion defines a bore, and the system further comprises:
a lock ring coupled to the head of the bone fastener and extending at least partially through the bore of the second portion.

21. The system of claim 20, wherein at least a portion of the lock ring cooperates with the first portion to limit the movement of the first portion relative to the second portion.

22. The system of claim 17, wherein the bone screw is rotatable about the longitudinal axis.

23. The system of claim 17, wherein the bone fastener is rotatable and pivotable relative to both the first portion and second portion of the saddle.

24. The system of claim 17, wherein the saddle is linearly movable in a predetermined direction relative to the coupling arrangement along the first axis.

25. The system of claim 17, wherein the coupling arrangement includes at least two components.

26. The system of claim 17, further comprising a rod having a longitudinal axis, the saddle defining a channel receiving the rod, the head of the bone fastener linearly movable relative to the rod in a direction perpendicular to the longitudinal axis of the rod.

27. The system of claim 26, wherein the head of the bone fastener is positionable between the channel and the second end of the bone fastener by linearly translating the coupling arrangement relative to the saddle in a direction perpendicular to a longitudinal axis of the rod.

28. The system of claim 17, wherein the bone fastener pivots relative to the coupling arrangement about a pivot axis, the pivot axis being linearly translatable with the coupling arrangement relative to the saddle in a direction perpendicular to the rod receiving axis.

29. The system of claim 17, wherein the first portion of the saddle includes first and second upwardly extending arms spaced apart in a lateral direction to define an opening for receiving the rod, the first portion of the saddle movable relative to the head of the bone fastener in the lateral direction.

30. The system of claim 29, wherein the first portion of the saddle is movable relative to the head of the bone fastener after assembly of the system.

31. A multiplanar bone anchor system for a fixation procedure comprising:
a bone fastener including a head and an end adapted to engage an anatomy;
a coupling arrangement coupled to the head of the bone fastener, the coupling arrangement further including a ring and a connecting arm, the ring having at least one wing, the ring coupled about at least a portion of the head of the bone fastener, the at least one wing of the ring coupling the ring to the connecting arm so that the ring rotates with the connecting arm; and a saddle including a first portion and a second portion, the first portion configured to receive a rod along a rod receiving axis, the first portion movable relative to the second portion in a direction perpendicular to the rod receiving axis, the bone fastener being pivotable and rotatable relative to the saddle, the saddle further including a third portion that includes at least one guide opposite at least one rail, the at least one guide of the first portion slidably coupled to the at least one rail of the third portion so that the first portion is movable relative to the third portion and the at least one rail of the second portion is slidably coupled to the at least one guide of the third portion so that the third portion is movable relative to the second portion;

wherein the second portion further comprises a bearing surface, and the at least one wing of the ring is coupled to the bearing surface to enable the bone fastener to rotate relative to the second portion, and;

wherein the at least one wing includes at least one taper, and the at least one taper cooperates with the bearing surface to enable the bone fastener to pivot about the head of the bone fastener.

32. A multiplanar bone anchor system for a fixation procedure comprising:

a bone fastener including a head and an end adapted to engage an anatomy;

a ring coupled about the head of the bone fastener, the ring including at least one wing;

a lock ring having a distal end coupled to the head of the bone fastener; and a saddle including a first portion and a second portion, the first portion configured to receive a rod along a rod receiving axis, the first portion of the saddle being coupled to the second portion of the saddle so as to be movable relative to the second portion in a direction perpendicular to the rod receiving axis, the second portion of the saddle coupled about the head of the bone fastener, the ring and at least a portion of the lock ring;

wherein the at least one wing of the ring cooperates with the lock ring and the second portion of the saddle to enable the bone fastener to pivot about the head of the bone fastener, and the at least one wing cooperates with the second portion to enable the bone fastener to rotate about the longitudinal axis relative to the saddle, and wherein the distal end of the lock ring includes at least one cut-out that cooperates with the at least one wing of the ring to enable the bone fastener to pivot about the head of the bone fastener.

33. The system of claim 32, wherein the saddle is linearly movable in a predetermined direction relative to the coupling arrangement.

34. The system of claim 32, wherein the coupling arrangement includes at least two components.

35. The system of claim 32, further comprising a rod having a longitudinal axis, the saddle defining a channel receiving the rod, the head of the bone fastener linearly movable relative to the rod in a direction perpendicular to the longitudinal axis of the rod.

36. The system of claim 35, wherein the head of the bone fastener is positionable between the channel and the second end of the bone fastener by linearly translating the coupling arrangement relative to the saddle in a direction perpendicular to the longitudinal axis of the rod.

37. The system of claim 32, wherein the bone fastener pivots relative to the coupling arrangement about a pivot axis, the pivot axis being linearly translatable with the coupling arrangement relative to the saddle in a direction perpendicular to the rod receiving axis.

38. The system of claim 32, wherein the first portion of the saddle includes first and second upwardly extending arms spaced part in a lateral direction to define an opening for receiving the rod, the first portion of the saddle movable relative to the head of the bone fastener in the lateral direction.

39. The system of claim 38, wherein the first portion of the saddle is movable relative to the head of the bone fastener after assembly of the system.

* * * * *